(12) United States Patent
Henkin et al.

(10) Patent No.: US 7,413,856 B2
(45) Date of Patent: Aug. 19, 2008

(54) IN VITRO TRANSCRIPTION ASSAY FOR T BOX ANTITERMINATION SYSTEM

(75) Inventors: Tina M. Henkin, Dublin, OH (US); Frank J. Grundy, Dublin, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 454 days.

(21) Appl. No.: 10/617,979

(22) Filed: Jul. 11, 2003

(65) Prior Publication Data

US 2004/0110187 A1    Jun. 10, 2004

Related U.S. Application Data

(60) Provisional application No. 60/395,081, filed on Jul. 11, 2002.

(51) Int. Cl.
  *C12Q 1/68* (2006.01)
  *C07H 21/00* (2006.01)
  *C12N 9/00* (2006.01)

(52) U.S. Cl. .............. 435/6; 536/23.1; 435/183

(58) Field of Classification Search .............. None
  See application file for complete search history.

(56) References Cited

U.S. PATENT DOCUMENTS 5,578,444 A * 11/1996 Edwards et al. .............. 435/6
6,022,983 A    2/2000 Wuonola et al.
6,174,722 B1 * 1/2001 Kirschbaum et al. ..... 435/320.1

FOREIGN PATENT DOCUMENTS

WO    2004/007677    1/2004

OTHER PUBLICATIONS

Henkin et al. Analysis of the *Bacillus subtilis* tyrS gene: conservation of a regulatory sequence in multiple tRNA synthetase genes. J Bacteriol. Feb. 1992;174(4):1299-306.*

Grundy et al. Specificity of tRNA-mRNA interactions in *Bacillus subtilis* tyrS antitermination. J Bacteriol. Apr. 1997;179(8):2587-94.*

Chopin et al. Analysis of the *Bacillus subtilis* genome sequence reveals nine new T-box leaders. Mol. Microbiol. Jul. 1998; 29(2):662-4.*

(Continued)

*Primary Examiner*—Young J. Kim
*Assistant Examiner*—Samuel Woolwine
(74) *Attorney, Agent, or Firm*—Calfee Halter & Griswold LLP

(57) ABSTRACT

A method and assay system is provided for screening for antimicrobial agents that inhibit or otherwise disrupt the transcription of bacterial aminoacyl-tRNA synthetases, particularly those in Gram-positive bacteria. The method and assay utilizes purified RNA polymerase, isolated, for example, from either *Bacillus subtilis* or *Escherichia coli*, and a template DNA fragment which encodes glycyl-tRNA synthetase, containing the promoter and leader region of the *B. subtilis* glyQS gene, including the T-Box terminator/antiterminator. Incubation in the presence of nucleotide triphosphates results in synthesis of an RNA transcript initiating at the glyQS promoter and terminating at the leader region terminator. Read-through of the terminator, and synthesis of an extended transcript, is dependent on addition of purified glycyl-tRNA. The method and assay is dependent on the use of the specified tRNA species; non-specific tRNA fails to stimulate antitermination. The assay can be used to screen for inhibitors that specifically inhibit the T-box antitermination mechanism.

32 Claims, 19 Drawing Sheets

OTHER PUBLICATIONS

Landick et al (1996). Quantitative analysis of transcriptional pausing by *Escherichia coli* RNA polymerase: his leader pause site as paradigm. Methods in Enzymology, vol. 274, pp. 334-353.*

Schimmel et al (1998). Aminoacyl tRNA synthetases as targets for new anti-infectives. The FASEB Journal, vol. 12, pp. 1599-1609.*

Luo et al. In vitro and in vivo secondary structure probing of the thrS leader in *Bacillus subtilis*. Nucleic Acids Research 26(23):5379-5387.*

Grundy, et al., "The T box and S box transcription termination systems", The Ohio State University, 1 page.

Gerdeman, et al., "Solution Structure of the *Bacillus subtilis* T-box Antiterminator RNA: Seven Nucleotide Bulge Characterized by Stacking and Flexibility", J. Mol. Biol. (2003) 326, pp. 189-201.

Yanofsky, "Transcription Attenuation: Once Viewed as a Novel Regulatory Strategy", Journal of Bacteriology, Jan. 2000 , pp. 1-8.

Gollnick et al., "Transcription attenuation", Biochimica et Biophysica Acta 1577 (2002) pp. 240-250.

Henkin, "Transcription termination control in bacteria", Current Opinion in Microbiology 2000, 3: pp. 149-153.

Barbieri et al., "MicroCorrespondence", 1998 Blackwell Science Ltd., Molecular Microbiology, 29, pp. 661-664.

van de Guchte, et al., "Identity elements in tRNA-mediated transcription antitermination: implication of tRNA D- and T-arms in mRNA recognition", Microbiology (2001), 147, pp. 1223-1233.

Kunst, et al., "The complete genome sequence of the Gram-positive bacterium *Bacillus subtilis*", Nature, vol. 390, Nov. 20, 1997, pp. 249-256.

Grundy, et al., "Sequence requirements for terminators and antiterminators in the T box transcription antitermination system: disparity between conservation and functional requirements", Nucleic Acids Research, 2002, vol. 30, No. 7, pp. 1646-1655.

Henkin, "Control of Transcription Termination in Prokaryotes,", Annu. Rev. Genet. 1996, 30: pp. 35-57.

Henkin, et al., "Regulation by transcription attenuation in bacteria: how RNA provides instructions for transcription termination/antitermination decisions", BioEssays 24: pp. 700-707.

Grundy et al., "The *Staphylococcus aureus ileS* Gene, Encoding Isoleucyl-tRNA Synthetase, Is a Member of the T-Box Family", Journal of Bacteriology, Jun. 1997, pp. 3767-3772.

Wagar, et al., "The Glycyl-tRNA Synthetase of *Chlamydia trachomatis*", Journal of Bacteriology, Sep. 1995, pp. 5179-5185.

International search report for PCT application No. PCT/US03/21875.

Gerdeman, et al, In vitro structure-function studies of teh *Bacillus subtillis* tyrS mRNA antiterminator: evidence, Nucleic Acids Research, vol. 30, No. 4, pp. 1065-1072, Feb. 2002.

Yousef, et al., tRNA requirement for glyQA antitermination: A new twist on tRNA, RNA, vol. 9, pp. 1148-1156, May 2003.

Grundy, et al., tRNA-mediated transcription antitermination in vitro: Codon-anticodon pairing independent of the ribosome, PNAS, vol. 99, No. 17, pp. 11121-11126, Aug. 2002.

Putzer, et al., Transfer RNA-mediated antitermination in vitro, Nucleic Acids Research, vol. 30, No. 14, pp. 3026-3033, 2002.

Sasero, et al., A *Bacillus subtilis* operon cntaining genes of unknown function senses tRNA trp charing and regulates expression, PNAS, vol. 97, No. 6, pp. 2656-2661, Mar. 2000.

Delorme, et al., Regulation of Expression of the *Lactococcus lactis* Histidine Operon, Journal of Bacteriology, vol. 181, No. 7, pp. 2026-2037, Apr. 1999.

Artsimovitch, I., et al., "RNA polymerases from *Bacillus subtilis* and *Escherichia coli* differ in recognition of regulatory signals in vitro", (2000) J. Bacteriol. 182, 6027-6035.

Grandoni, J. A., et al., "Regions of the *Bacillus subtilis* ilv-leu Operon involved in regulation by Leucine" (1993) J. Bacteriol. 175, 7581-7593.

Grundy, F. J., et al., "Interaction between the acceptor end of tRNA and the T box stimulates antitermination in the *Bacillus subtilis* tyrS gene: a new role for the discriminator base" (1994) J. Bacteriol. 176, 4518-4526.

Grundy, F. J., et al., "tRNA determinants for transcription antiterminatin of the *Bacillus subtilis* tyrS gene". (2000) RNA 6, 1131-1141.

Grundy et al., "Monitoring uncharged tRNA during transcription of the *Bacillus subtilis* glyQS Gene", (2005) J Mol Biol, 346, 73-81.

Hager, D. A., et al., "Use of mono Q high-resolution ion-exchange chromatography to obtain highly pure and actdive *Escherichia coli* RNA polymerase", (1990) Biochemistry 29, 7890-7894.

Hurwitz et al., "The intracellular concentration of bound and unbound magnesium ions in *Escherichia coli*", (1967) J of Biol. Chemistry, 242, 3719-3722.

Landick, R., Turnbough, C. L., Jr., & Yanofsky, C. (1996) in *Escherichia coli* and *Salmonella*: Cellular and Molecular Biology, eds. Neidhardt, F. C., Curtis, R., III, Ingraham, J. L., Lin, E. C. C., Low, K. B., Magasanik, B., Reznikoff, W. S., Riley, M., Schaecter, A. & Umbarger, H. E. (Am. Soc. Microbiol., Washington, DC), 1263-1286.

Luo, D., et al., "In vitro and in vivo secondary structure probing of the thrS leader in *Bacillus subtilis*", (1998) Nucleic Acids Res. 26, 5379-5387.

Nelson et al., "tRNA regulation of gene expression: Interactions of an mRNA 5'-UTR with a regulatory tRNA", (2006) RNA, 12, 1-8.

Qi, Y. & Hulett, F. M. "PhoP~P and RNA polymerase δA holoenzyme are sufficient for transcription of Pho regulon promoters in *Bacillus subtilis*: PhoP~P activator sites within the coding region stimulate transcription in vitro", (1998) Mol. Microbiol. 28, 1187-1197.

Rollins, S. M., et al., "Analysis of cis-acting sequence and structural elements required for antiterminatin of the *Bacillus subtilis* tyrS gene", (1997) Mol. Microbiol. 25, 411-421.

Winkler, W. C., et al., "The GA motif: an RNA element common to bacterial antitermination systems, rRNA, and eukaryotic RNAs", (2001) RNA 7, 1165-1172.

Yousef et al., "Structural transitions induced by the interaction between tRNAGLY and the *Bacillus subtilis* glyQS T box leader RNA", (2005) J Mol Biol, 349, 273-287.

Henkin et al., "Sensing Metabolic Signals with nascent RNA transcripts: the T-box and S-box riboswitches as paradigms", (2007) Cold Spring Harbor Symposia on Quantitative Biology, vol. LXX1, 1-7.

Grundy, F. J. & Henkin, T. M. "tRNA as a positive regulator of transcription antitermination in *B. subtilis*", (1993) Cell 74, 475-482.

Anagnostopoulos, C. & Spizizen, J. "Requirements for Transformation in *Bacillus subtilis*", (1961), J. Bacteriol. 81, 741-746.

Ban et al., "The Complete Atomic Structure of the Large Ribosomal Subunit at 2.4 A Resolution", (2000) Science 289, 905-920.

Friedman, D. I. & Court, D. L. "Bacteriophage lambda: alive and well and still doing its thing", (2001) Curr. Opin. Microbiol. 4, 201-207.

Giege et al., "Universal rules and idiosyncratic features in tRNA identity", (1998) Nucleic Acids Res. 26, 5017-5035.

Grundy et al., "Regulation of the *Bacillus subtilis* Acetate Kinase Gene by CcpA", (1993) J. Bacteriol, 175, 7348-7355.

Ogle et al., "Recognition of Cognate Transfer RNA by the 30S Ribosomal Subunit", (2001) Science 292, 897-902.

Qiu et al., "The tRNA-binding moiety in GCN2 contains a dimerization domain that interacts with the kinase domain and is required for tRNA binding and kinase activation", (2001) EMBO J. 20, 1425-1438.

Rhodes, G. & Chamberlin, M. J. "Ribonucleic Acid Cain Elongation by *Escherichia coli* Ribonucleic Acid Polymerase", (1974) J. Biol. Chem. 249, 6675-6683.

Sankaranarayanan et al., "The Structure of Threonyl-tRNA Synthetase-tRNA Complex Enlightens Its Repressor Activity and Reveals an Essential Zinc Ion in the Active Site", (1999) Cell 97, 371-381.

Treiber, D. K. & Williamson, J. R. "Beyond kinetic traps in RNA folding", 82, 221-230.(2001) Curr. Opin. Struct. Biol. 11, 309-314.

Weeks, K. M. & Cech, T. R. "Protein Facilitation of Group I Intron Splicing by Assembly of the Catalytic Core and the 5' Splice Site Domain", (1995) Cell 82, 221-230.

Guerrier-Takada et al., "The RNA Moiety of Ribonuclease P Is the Catalytic Subunit of the Enzyme", (1983) Cell 35, 849-857.

* cited by examiner

FIG. 3: Panel A

```
B.sub tyrS   AGCTTCATATGAAAAGGTAAAGATTGAGA---CAAGTAGA-ATATCCT------------TACGT-----TCCAGAGA--GCT---GAT
B.ant glyS   ATTATTAATATAAGTAGCGATGACGGACT-TATAAGTACTTGC------------------ACA-----AAAAGCGA--TTC---AGG
B.cer glyS   ATTATTAATATAAGTAGCGATGACGGACT-TATAAGTACTTGC------------------ACA-----AAAAGCGA--TTC---AGG
B.hal glyS   AATGTTATATTTCAATGCTATGACGGAGA---ACAGTACTTGATTCCT----------TTTACAT-----AAAAGCGA--ACC---TAG
B.ste glyS   AAATCATATATGGATCGCGATGACGGATC--AATAGTAGTTAACCCTC------------TCTTC-----CCAAGCGA--GCC---GGG
B.sub glyS   TATTATTAAATATGTTGCAGTGAGAGAAA---GAAGTACTTGCGTTTA-----------CCTCAT-----GAAAGCGA--CCT---TAG
C.ace glyS   ATAATTTAATATCTATACAATGACAAAGAT----AGAAATTGTATTTT--------------CTT-----CAAAGAGA--GGC---TGT
C.hyd glyS   AATTAATAATGGATTGGCAGTGAACCGGA---GGAGTAGCTGTGATTT-------------CCCT-----TAAAGAGA--GCC---GGG
D.rad glyS   ------------GGAGGCGTTGAACCGCA---GGAGTACCG-CGAAGA----------GCCCCCA-----ACGAGCGA--GCC---TGA
E.fae glyS   GAGAAGTTAAATACGTACGAAGAAAAAGA---GAAGTAAAAAGAACCC-----------TCTGTT-------AAGCGAA-TCT----GG
L.lac glyS   GCCTTGACAAAATGGGAAAATAGAGCTAG------AATTTATA-------------------GGT-----------AGCGA--CTC---GAA
L.mon glyS   ATATCAACTAATAGGTACGTTGAAGGAAA---ATAGTAACAAAAAGCT------------CT-AT----TTTTAGCGA--GTC---CGG
S.aur glyS   ATGTCACAAACACATTAATTTTACTTGCC--TTTAAATAATCTATCAA---------------TT---*GTACAGCGA--GTT---AAG
S.equ glyS   TTTGTGATAAACTAACCAATAG-GAAAGA---------AAATAGCAGG---------TTTCTGATC-----TAAAGCGA--GCT---CGG
S.mut glyS   ------------------GTTAAGAAAGA--------GAGT--TTTGT---------GGCGTTTC-----TGCAGCGA--ACC---TGA
S.pne glyS   ATTTTTGATATAATAGTCAGCAGGAAAGA--------AAGTCTT--AT---------GGCGTTCT-----TCAAGCGA--GCT---TGG
S.pyo glyS   GCTTTATGCTAAACTAGACTCTAGGAAAA---------AGGATGCAAG--------TATCTTATC-----TAAAGCGA--GTT---CGG
```

FIG. 3: Panel B

```
B.sub tyrS   ---GGCCGGTGAAA--ATC---AGCACAGA------------CGGATATATC--GAA---TACA--CTCATGAACC------------
B.ant glyS   ----GATAGTGAAAG-CCT---GAAGCC------------------GCAAG--GAA-ACGGCA--GTCTCGAGC-------------
B.cer glyS   ----GATAGTGAAAG-CCT---GAAGCC------------------GCAAG--GAA-ACGGCA--GTCTCGAGC-------------
B.hal glyS   ----GATGGTGAGAG-CTA---GGGATGTAAA-------------CATCAAG--GAA---GGCA--CTCTTGAGCA-TGAA--------
B.ste glyS   ----GACGGTGGAAG-CCC---GGCGAAGA--------------TGGTTAAT--GAA-ACGGCA--GTCCGGAGCG------------
B.sub glyS   ----GGCGGTGTAAG-CTA---AGGATGAG--------------CACGCAAC--GAA--AGGCA--TTCTTGAGCAA-----------
C.ace glyS   ---GGAGGGTGTAA--ACG---GTCAAG----------------AAAATTCAGT--AGT---GGAG-TCTTTCGAGTA------------
C.hyd glyS   ---GGCTGGTGTGA--ACC---GGTAGGG---------------A-TAAACGGT--GAA---GGCG--CCGGGAGCCG-----------
D.rad glyS   ----GACGGTGAGAG-TCA---GGCAGGGTGA-------------GGCGCGACGG--GAA--AGGCA--GCGGGAGCC------------
E.fae glyS   ----GAGAGTGGGAG-CC----AGAAACA----------------CGGAACTTTT--GAA--AGGCA--CTTTGGAGTACG----------
L.lac glyS   ----GATAGTGAAAG-TTC---GAGAAC-----------------------AATAA--T-----GGCT  TAACTT----------------
L.mon glyS   ----GTTTGGTGTGAG-CCG---GATATTTA-----------ACTTTTTTGT--GAA---GGCG--TTCTGGAGTA------------
S.aur glyS   ----GATAGTGTAAG-CTT---AACAA-----------------T---AAGATT--------GGC---GCAACGAATC------------
S.equ glyS   ---GGCTGGTGAGAG-CCG---AGTGAT-GG--T--------ACTGCTGGTT--------GGCG--CTTTCTCTA-------------
S.mut glyS   ----GAGAGTGTAAG-TCA---GGTGAAACAAA---------ATAAAGGACT--------GGCA  CTTTCT----------------
S.pne glyS   ----GATAGTGGGAG-CCA---AGTAGGCAAA----------ATAAAGGGCT--------GGCG--CTTTCT----------------
S.pyo glyS   ----GGTAGTTAGAG-CCG---AATGGTAGGA------------CTGCAGATT--------GGCG--CTTCCGTTT-------------
```

FIG. 3: Panel C

```
B.sub tyrS   GCT----------TTTGC--AAAC--AAAGCC--------GGCCA------GGCTTT-----CAGTA---GTGAA-----------AGA
B.ant glyS   ------------------------------------AATACGTGATAA------------------------------------------
B.cer glyS   ------------------------------------AATACGTGATAA------------------------------------------
B.hal glyS   ------------------------------------CGATGAAAAGAA------------------------------------------
B.ste glyS   ------------------------------------GAAATGGCAAAA------------------------------------------
B.sub glyS   ------------------------------------------------------------------------------------------
C.ace glyS   TTT-------------TT---------------------AAAA-------------------------GA-------------AAA
C.hyd glyS   GCA-------------GGAGGAAA--CCC-----------CAAG---------GGG-----AGTAAAGCC-------------TGC
D.rad glyS   ------------------------------------------------------------------------------------------
E.fae glyS   ------------------------------------------------------------------------------------------
L.lac glyS   ----------AAAACTGTAATGAAC---------------ACAAAT--------------AAAGTAAAAA-----------------
L.mon glyS   ------------------------------------CAGCGAAATCAA------------------------------------------
S.aur glyS   -----------------------------------ATTTTAAAATAAA------------------------------------------
S.equ glyS   -----------------------------------AAGAGTAGGCTCA------------------------------------------
S.mut glyS   CTT-----------GGCT----------------------AAT--------------------------AGCC-------------AAG
S.pne glyS   ------------------------------------------------------------------------------------------
S.pyo glyS   GGG--CAGTGT-GATTAAG---------------------TATA-------------------------TTT-GTCAATATTG--CCC
```

FIG. 3: Panel D

```
B.sub tyrS   -ACGGA----------CCTGA-----TCCGTTATCAGG----------------------------------------------------
B.ant glyS   ------------------------------------------------------------------------------------------
B.cer glyS   ------------------------------------------------------------------------------------------
B.hal glyS   ------------------------------------------------------------------------------------------
B.ste glyS   ------------------------------------------------------------------------------------------
B.sub glyS   ------------------------------------------------------------------------------------------
C.ace glyS   --GC---------------AGG-------GCTATTGCC---------------------------------------------------
C.hyd glyS   ------------------------------------------------------------------------------------------
D.rad glyS   ------------------------------------------------------------------------------------------
E.fae glyS   ------------------------------------------------------------------------------------------
L.lac glyS   ------------------------------------------------------------------------------------------
L.mon glyS   ------------------------------------------------------------------------------------------
S.aur glyS   ------------------------------------------------------------------------------------------
S.equ glyS   ------------------------------------------------------------------------------------------
S.mut glyS   ------------------------------------------------------------------------------------------
S.pne glyS   ------------------------------------------------------------------------------------------
S.pyo glyS   ------------------------------------------------------------------------------------------
```

FIG. 3: Panel E

```
B.sub tyrS  ------------------------------------TAAGACGAATGTTG------------CATTC-TCTTA-----------TTA
B.ant glyS  ----------------AAAGTGA-------------------------------GCACCTTTT-------GTGT----------------ATC
B.cer glyS  ----------------AGTGGAT-------------------------------GCACCTTTT-------GTGT----------------ATC
B.hal glyS  ----------------AGTGGAT-------------------------------TATGGTGTC-------ATCATA--------------GGC
B.ste glyS  ----------------AGTGGCC-------------------------------GCGTGATT--------TGCGC---------------ATC
B.sub glyS  ----------------AGGGGAT-------------------------------GGGATTTTGT------TCTC----------------AGC
C.ace glyS  --------TTTTAAAAAGAGGCT------------------------------------------------G-------------------
C.hyd glyS  ----------AGAGTTTGAGGTGGGC----------------------CTTTTTT--------------------G---------------GCC
D.rad glyS  ACAACCGGTCTGAAAGGTGCTG--------------------------GCGAGG---------------GC-------------------CAG
E.fae glyS  ------------ACAAACGAAGCT-----------------------GCCGATGAACA----------CATCGG----------------AAG
L.lac glyS  ------------------------------------------------------------------------------------------G
L.mon glyS  ----------------GGTGGGA-----------------------------ATTGTTT---------TAAT------------------TCC
S.aur glyS  ----------------AGCGAGT-------------------------------GACTA----------C--------------------ACT
S.equ glyS  ----------------GGTGTTT----------GTAGCTTGCTTGACATCTGTT-------------TATCAA-CAAG-ATC--------AAA
S.mut glyS  ----------------CTAACA------------------------------ATCAGATAAA-------TGA------------------AGT
S.pne glyS  ----------------GTAGTAT---------------------------T--TTCAAAACAA------TGAAGTA--------------ATA
S.pyo glyS  ---------AAAAGATAC------------------------------TATATAAA------------TGAA------------------GTA
```

FIG. 3: Panel F

```
B.sub tyrS  ---GTAGGGTGGTACCGCGAT----AATCA--------------ATCGT-----CCCT-
B.ant glyS  ---AACTAGGGTGGAACCGCGGGC--AAAC----------------GCTCGT-----CCCTAG-
B.cer glyS  ---AACTAGGGTGGAACCGCGGGC--AAAC----------------GCTCGT-----CCCTAG-
B.hal glyS  ---AAATAGGGTGGAACCGCGGGG--TTAACT---------------CTCGT-----CCCTAT-
B.ste glyS  ---AACTAGGGTGGAACCGCGGGAGC-TAC----------------GCTCTCGT---CCCTAG-
B.sub glyS  ---AACTAGGGTGGAACCGCGGGA--GAAC----------------TCTCGT-----CCCTA-
C.ace glyS  ---AATAAGGGTGGAACCGCGGAA--GTAA-----------------TTTCGT-----CCCTT-
C.hyd glyS  ---AACCAGGGTGGAACCGCGAAGG-ATGCC----------------CCTTCGT----CCCTGG-
D.rad glyS  ---AACTGGGGTGGAACCGCGCATG-TCC------------------CGTGCGT----CCCCGG-
E.fae glyS  -----TAGGGTGGAACCGCGCGA---TAATTAT--------------TCGT-------CCCTA-
L.lac glyS  ---ATAAAGGTGGAACCGCGTGC---ATTT-----------------GCAC-------CCTTTGT
L.mon glyS  ---AAATAGGGTGGAACCGCGAG---CTAACT---------------CTCGT-----CCCTAT-
S.aur glyS  ---AATTGGGTGGAACCGCGGGT*---------------------AACTCGT----CCCA--
S.equ glyS  TGAAGTAATAATTAGGGTGGAACCGCGGCGT-TTTG----------ACGC-----CCCTA-
S.mut glyS  ---AATAAATTAGGGTGGAACCGCGGTT-TCA---------AACGC-----CCCTA-
S.pne glyS  ---AATTAGGGTGGAACCGCGCGTT-TCT----------GACGC-----CCCTAG-
S.pyo glyS  ---ATAAATTAGGGTGGAACCGCGT-TTTG---------ACGC-----CCCTAG-
```

FIG. 4

| Organisms with Leader Sequences Having the T Box Pattern | NCBI Genome Sequence File Name |
|---|---|
| *Bacillus anthracis* | NC_003997 |
| *Bacillus cereus* | NC_004722 |
| *Bacillus halodurans* | NC_002570 |
| *Bacillus subtilis* | NC_000964 |
| *Carboxydothermus hydrogenoformans* | NC_002972 |
| *Clostridium acetobutylicum* | NC_003030 |
| *Clostridium botulinum* | NC_003223 |
| *Clostridium difficile* | NC_002933 |
| *Clostridium perfringens* | NC_003366 |
| *Clostridium tetani* | NC_004557 |
| *Clostridium thermocellum* | NZ_AABG00000000 |
| *Corynebacterium glutamicum* | NC_003450 |
| *Corynebacterium diptheriae* | NC_002935 |
| *Deinococcus radiodurans* | NC_001263 |
| *Desulfitobacterium hafniense* | NZ_AAAW00000000 |
| *Enterococcus faecalis* | NC_004668 |
| *Enterococcus faecium* | NZ_AAAK00000000 |
| *Geobacillus stearothermophilus* | NC_002926 |
| *Geobacter sulfurreducens* | NC_002939 |
| *Lactococcus lactis* | NC_002662 |
| *Leuconostoc mesenteroides* | NZ_AABH00000000 |
| *Listeria innocua* | NC_003212 |
| *Listeria monocytogenes* | NC_003210 |
| *Mycobacterium leprae* | NC_002677 |
| *Mycobacterium tuberculosis* | NC_000962 |
| *Oceanobacillus iheyensis* | NC_004193 |
| *Oenococcus oeni* | NZ_AAAZ00000000 |
| *Ruminococcus albus* | NC_003373 |
| *Spiroplasma kunkelii* | NC_003999 |
| *Staphylococcus aureus* | NC_002758 |
| *Staphylococcus epidermidis* | NC_004461 |
| *Streptococcus equi* | NC_002955 |
| *Streptococcus gordoniae* | NC_002979 |
| *Streptococcus mutans* | NC_004350 |
| *Streptococcus pneumoniae* | NC_003098 |
| *Streptococcus pyogenes* | NC_002737 |
| *Streptomyces coelicolor* | NC_003888 |
| *Thermoanaerobacter tengcongensis* | NC_003869 |
| *Thermobifida fusca* | NZ_AAAQ00000000 |

FIG. 5
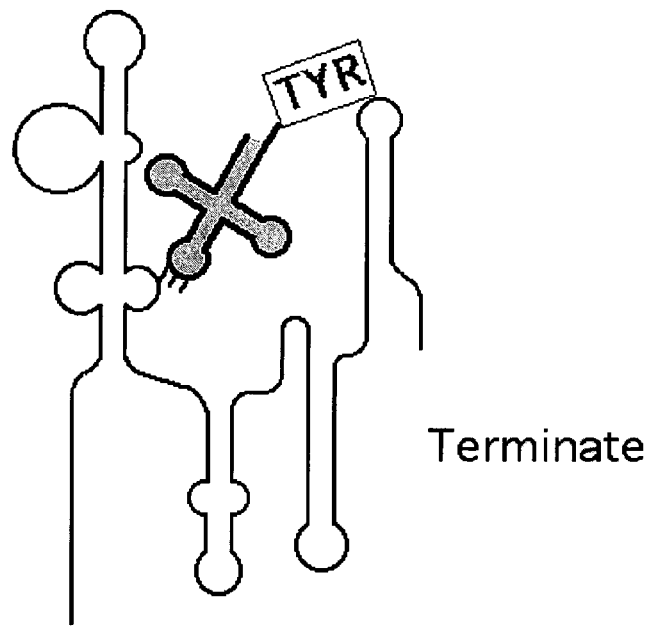
High tRNA charging
Terminate
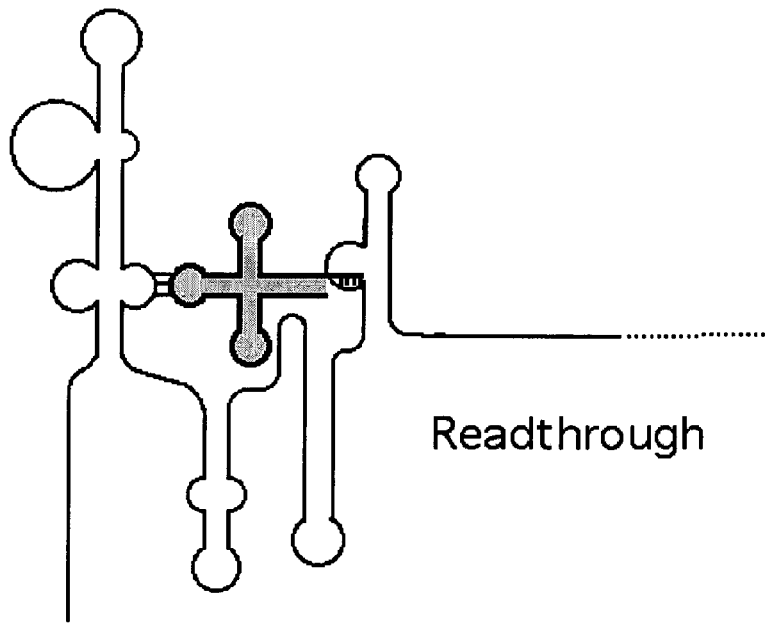
Low tRNA charging
Readthrough

FIG. 11

Polynucleotide sequence for the *glyQS* gene from *Bacillus subtilis* corresponding to the *in vitro* transcription template: from *B. subtilis* 168.

```
ATTGATTTATATTACGAAGAATATTCGGGATTGTATTTAAAATCAAAGCGCTTTTTAGATCAAATGGAAAGCATGAA
ACATCTTATGGGTGAAAACAAAAGTTGACATTTGGTCCATCTTTTTATATGATCATTTATTATTAAATATGTTGCAG
TGAGAGAAAGAAGTACTTGCGTTTACCTCATGAAAGCGACCTTAGGGCGGTGTAAGCTAAGGATGAGCACGCAACGA
AAGGCATTCTTGAGCAATTTTAAAAAAGAGGCTGGGATTTTGTTCTCAGCAACTAGGGTGGAACCGCGGGAGAACTC
TCGTCCCTATGTTTGCGGCTGGCAAGCATAGAGACGGGAGTTTTTTGGTTGCTGCCGCAGTCAACTTATGAAAGAAA
AGTGGAGGTGCTTGAAATGAATATTCAAGACATGATTCTAACCTTGCAAAAGC
```

FIG. 12

Sequence of same region from BR151MA (T to A at +6 position relative to transcription start-site)

ATTGATTTATATTACGAAGAATATTCGGGATTGTATTTAAAATCAAAGCGCTTTTTAGATCAAATGGAAAGCATGAA
ACATCTTATGGGTGAAAACAAAAGTTGACATTTGGTCCATCTTTTTATATGATCATTTATTATAAAATATGTTGCAG
TGAGAGAAAGAAGTACTTGCGTTTACCTCATGAAAGCGACCTTAGGGCGGTGTAAGCTAAGGATGAGCACGCAACGA
AAGGCATTCTTGAGCAATTTTAAAAAAGAGGCTGGGATTTTGTTCTCAGCAACTAGGGTGGAACCGCGGGAGAACTC
TCGTCCCTATGTTTGCGGCTGGCAAGCATAGAGACGGGAGTTTTTTGGTTGCTGCCGCAGTCAACTTATGAAAGAAA
AGTGGAGGTGCTTGAAATGAATATTCAAGACATGATTCTAACCTTGCAAAAGC

FIG. 13 tRNA<sup>Gly</sup> DNA sequence: (from SubtiList, confirmed by sequencing of region in BR151MA)

GCGGAAGTAGTTCAGTGGTAGAACACCACCTTGCCAAGGTGGGGGTCGCGGGTTCGAATCCCGTCTTCCGCTCCA

FIG. 14

PCR primers used for preparing *glyQS* template:

GlyQUS1Xba: ATTGATCTAGATTACGAAGAATATTCGGGATTGTA (contains two changes from sequence shown in Fig. 12 to introduce an XbaI site (TCTAGA) at the 5' end of the fragment for generation of the *glyQS-lacZ* fusion construct)

GlyQDS2H3Pac: GGGTATTTAATTAAGCTTTTGCAAGGTTAGAATCA (introduces extra 14 nt downstream of *glyQS* sequence shown in Fig. 12 to provide a HindIIIsite (AAGCTT) for generation of the *glyQS-lacZ* fusion construct)

The PCR primers used to generate the *tyrS* template:

TyrUSBM: GGCTGGGGATCCGTCAACAATGGAGG
TyrN2b: CCGCGGAAGGATAAAGCTTCAAGTAAG

FIG. 15

Polynucleotide sequence for the *tyrS* template DNA (identical for 168 or BR151MA).

```
GGCTGGAGATCTGTCAACAATGGAGGATTAAAAGGCGGCGTTGACACAGGATTTTATTTATGTTAAAAATGATATAG
CTTCATATGAAAAGGTAAAGATTGAGACAAGTAGAATATCCTTACGTTCCAGAGAGCTGATGGCCGGTGAAAATCAG
CACAGACGGATATATCGAATACACTCATGAACCGCTTTTGCAAACAAAGCCGGCCAGGCTTTCAGTAGTGAAAGAAC
GGACCTGATCCGTTATCAGGCAAAGTGATAAGACGAATGTTTGCATTCTCTTATTAGTAGGGTGGTACCGCGATAAT
CAATCGTCCCTTCGTGTAAACGAAGGGGCGTTTTTTATTTTAATTAAAAAAGGAGCTTTATCTTATGACTAACTTAC
TTGAAGACTTATCCTTCCGCGG
```

FIG. 16

The oligos used to generate tRNA<sup>Tyr</sup>:

```
5': TyrUSBM:    GGCTGGGGATCCGTCAACAATGGAGG
3': TyrN2b:     CCGCGGAAGGATAAAGCTTCAAGTAAG

5': tRNATyrUST7: TAATACGACTCACTATAGGAGGGGTAGCG  (the tRNA sequence
starts with GGAGGGGTAGCG)
3': tRNATyrDS:   TGGTGGAGGGGGCAGATTCG
```

The oligos used to generate tRNA<sup>Gly</sup>:

```
5': GlytRNAUS:   TAATACGACTCACTATAGCGGAAGTAGTTCAGTGG
(the first part of this oligo is the T7 promoter; the tRNA starts
with GCGGAAGTAGTTCAGTGG)
3': GlytRNADS:   TGGAGCGGAAGACGGGATTCGAAC
```

FIG. 17 tRNA<sup>Tyr</sup> DNA sequence.

GGAGGGGTAGCGAAGTGGCTAAACGCGGCGGACTGTAAATCCGCTCCCTCAGGGTTCGGCAGTTCGAATCTGCCCCC
CTCCACCA

IN VITRO TRANSCRIPTION ASSAY FOR T BOX ANTITERMINATION SYSTEM

CROSS REFERENCE TO RELATED APPLICATIONS

This application claims the benefit of the filing date of U.S. Provisional Application No. 60/395,081, filed Jul. 11, 2002, which is incorporated herein by reference in its entirety.

STATEMENT ON GOVERNMENT FUNDED RESEARCH

The present invention was made, at least in part, with support from the National Institutes of Health Grant GM47823. The United States Government has certain rights in the invention.

BACKGROUND

Aminoacyl-tRNA synthetases are enzymes found in all bacteria, plants and animals, and are required for cells to make protein. Bacterial aminoacyl-tRNA synthetases are usually present as a single species for each amino acid; approximately 20 different synthetases are required for aminoacylation. Lacking redundancy in the aminoacylation step of protein synthesis, bacteria are critically dependent on the transcription and translation of each of these enzymes. Inhibitors that block the production or function of one or more bacterial synthetases are therefore potentially useful as antimicrobial agents for prevention and treatment of disease in humans and other organisms.

A potential target for shutting-down expression of bacterial aminoacyl synthetase genes is the T-box termination/antitermination transcriptional control complex. Many Gram positive, and certain Gram negative bacteria have genes that are regulated by a transcriptional control element known as the T-box termination/antitermination complex. This complex comprises a set of specific control elements that are found within the leader sequences located upstream of certain bacterial genes. The structural arrangement of these leaders is conserved across a broad spectrum of bacterial strains, and the control elements that are specific to the T-box termination/antitermination complex are highly conserved. The T-box termination/antitermination complex regulates expression of aminoacyl-tRNA synthetase genes and other amino acid-related genes in response to the level of charging of cognate tRNAs. Uncharged tRNAs permit read-through of the template by favoring the antiterminator configuration, thus resulting in expression of the gene located downstream of the leader region. Charged tRNAs block read-through of the template by favoring the terminator configuration, thus resulting in termination of expression. Since expression of these T-box regulated genes is required for survival of the bacterial cell, and this system is found in many pathogenic organisms, the T box system represents a target for antimicrobial agents. To date, it has not been possible to isolate this complex in a cell-free system in order to evaluate potential specific modulators or inhibitors of expression of T-box regulated genes. Thus, it would be useful to have a well-defined in vitro assay that would permit evaluation of agents that specifically interact with the T-box termination/antitermination complex. Such an assay system would permit the rapid and high throughput screening of potential inhibitors of expression of T-box regulated genes.

SUMMARY

An in vitro screening assay is provided for identifying inhibitors of transcription of T-box regulated genes. An in vitro transcription assay system is also provided and comprises a template DNA (comprising a bacterial promoter, a leader region of a T-box-regulated gene (such as the *B. subtilis* glyQS gene), and a downstream portion), a cognate tRNA which is specific for the specifier sequence of the template DNA (such as *B. subtilis* tRNA$^{Gly}$), and bacterial RNA polymerase. Combining a test agent with the assay system permits the detection of potential inhibitors which function to block antitermination in the T-box region, and thus cause termination of transcription and loss of expression of T-box regulated genes.

The screening assay comprises the steps of: (a) incubating template DNA and cognate tRNA, RNA polymerase, a divalent metal cation, such as magnesium ($Mg^{2+}$), nucleoside triphosphates (singularly referred to as "NTP," including adenosine triphosphate, or ATP, guanosine triphosphate, or GTP, cytosine triphosphate, or CTP, and uridine triphosphate, or UTP), and a dinucleotide which corresponds to the dinucleotide encoded by the transcription start site in the leader, such as ApU, ApC, etc., both with and without a test agent which is a potential inhibitor; (b) assaying for mRNA transcription in the system; and (c) comparing the results obtained in the absence verses the presence of the test agent.

The screening assay is useful for rapid, high volume screening of substances that inhibit T-box regulated antitermination of transcription in bacteria which rely upon the T-box control mechanism, and more particularly in Gram-positive bacteria. This inhibition effectively terminates transcription of T-box regulated genes, such as glycyl-tRNA synthetase, restricting the availability of the gene product and thereby interrupting bacterial protein production and bacterial viability. In addition to inhibition of T-box regulated genes such as glycyl- and other aminoacyl-tRNA synthetases, such inhibitors may also inhibit expression of other T-box regulated genes. The identified inhibitors would be useful agents for applications where antimicrobials are desired, such as in the treatment of bacterial infections and related disease in humans and other affected organisms. Thus, the screening assay is useful for identifying potential antimicrobial agents, including antibiotics.

BRIEF DESCRIPTION OF THE DRAWINGS

FIG. 3 shows a structure-based alignment of glyQS leaders, including the T-box sequence, from several bacterial strains (SEQ ID NOS 3-19, respectively in order of appearance); the *B. subtilis* tyrS leader is shown at the top, for comparison. The sequences are aligned based on major domains, as follows: Panel A: 5' side of Stem I; Panel B: 3' side of Stem I; Panel C: Stem II (replaced by an unpaired stretch in most of the glyQS leaders); Panel D: Stem IIA/B (missing in most of the glyQS leaders); Panel E: Stem III; Panel F: antiterminator. The specifier in each sequence is indicated in bold (TAC for tyrS and GGC for glyQS). (Key: B. sub: *Bacillus subtilis*; B. ant: *Bacillus anthracis*; B. cer: *Bacillus cereus*; B. hal: *Bacillus halodurans*; C. ace: *Clostridium acetobutylicum*; C. hyd: *Carboxydothermus hydrogenoformans*; D. rad: *Deinococcus radiodurans*; E. fae: *Enterococcus faecalis*; L. lac: *Lactococcus lactis*; L. mon: *Listeria monocytogenes*; S. aur: *Staphylococcus aureus*; S. equ: *Streptococcus equi*; S. mut: *Streptococcus mutans*; S. pne: *Streptococcus pneumoniae*; and S. pyo: *Streptococcus pyogenes*).

The dashes represent spaces inserted to permit alignment of all of the T box leaders (not just tyrS/glyQS); the leaders are variable in having helical domains of different lengths, and insertions/deletions/replacements at various positions, however, the overall pattern is highly conserved. The alignments start at the 5' side of the base of Stem I; the distance from the transcription start-site is variable, but is usually around 20-30 nt. In some cases, the T box structure is embedded within a larger transcriptional unit, so that the 5' portion of the mRNA is constitutively transcribed and the gene encoded is constitutively expressed; in those cases, the T box element controls expression of the 3' transcriptional units. Accordingly, there are no specific requirements as to how much sequence is upstream of the structural array shown in the alignment.

FIG. 4 is a list of bacterial strains in which T-box regulated genes have been identified.

FIG. 5 shows a model of the T box antitermination mechanism actuated by a cognate uncharged tRNA. When the cognate tRNA is efficiently charged, read-through is blocked by formation of the terminator helix. When the cognate tRNA is not efficiently charged, read-through is permitted by formation of the antiterminator structure.

Figure 6:
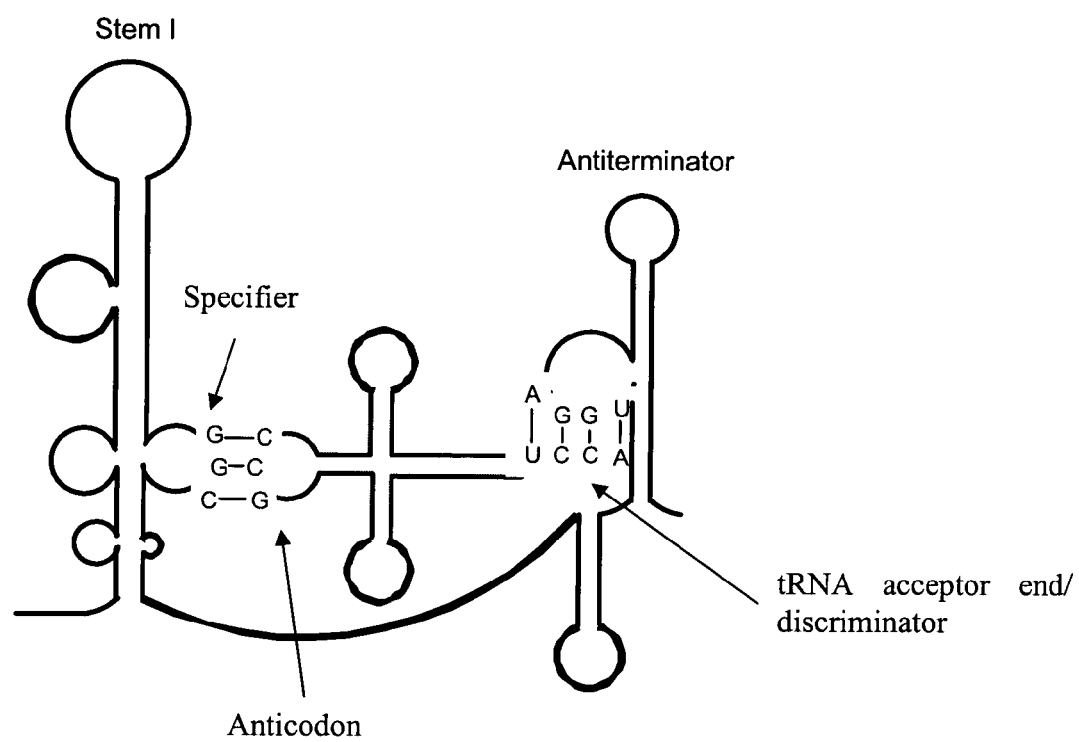

FIG. 6 shows a model of interaction of a T-box leader in the antiterminator conformation with a cognate uncharged tRNA.

Figure 7:
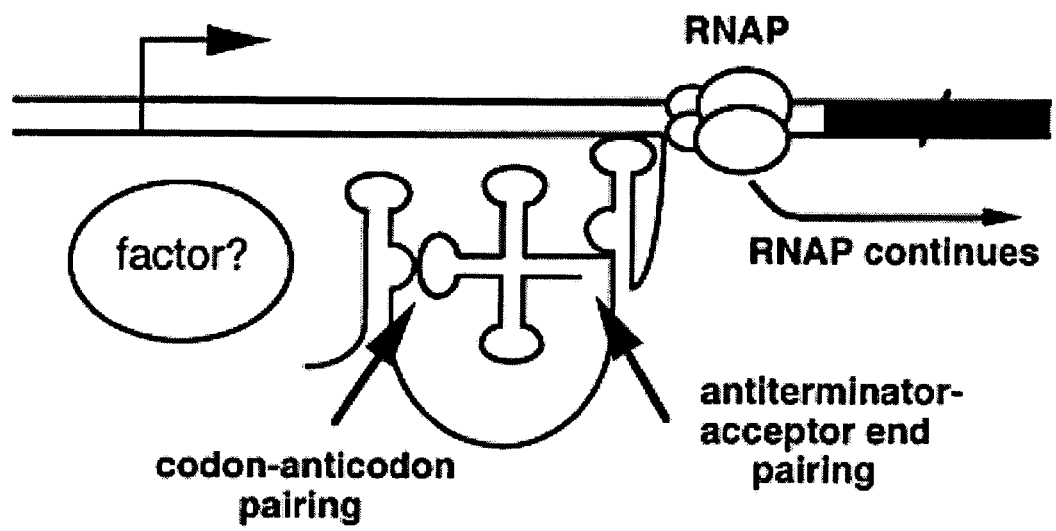

FIG. 7 shows a model of the T box antitermination mechanism. The arrow indicates the transcription initiation site. The black rectangle represents the coding region of the regulated gene. Uncharged tRNA is postulated to interact with the nascent transcript at both the specifier sequence (a codon specific for the target gene) and the antiterminator bulge, stabilizing the antiterminator and preventing formation of the competing terminator structure. RNA polymerase (RNAP) then continues past the terminator region, and the full-length transcript is synthesized. "Factor?" indicates putative factor(s) that could modulate the leader RNA-tRNA interaction in vivo.

Figure 8:
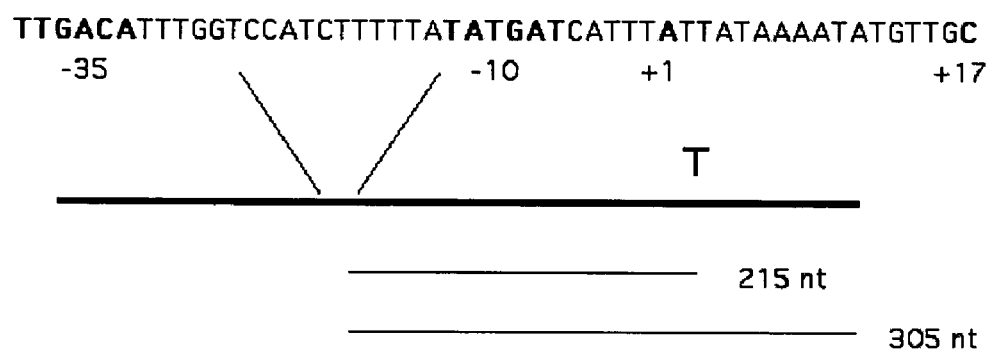

FIG. 8 shows the glyQS promoter region map (SEQ ID NO: 20).

Figure 9:
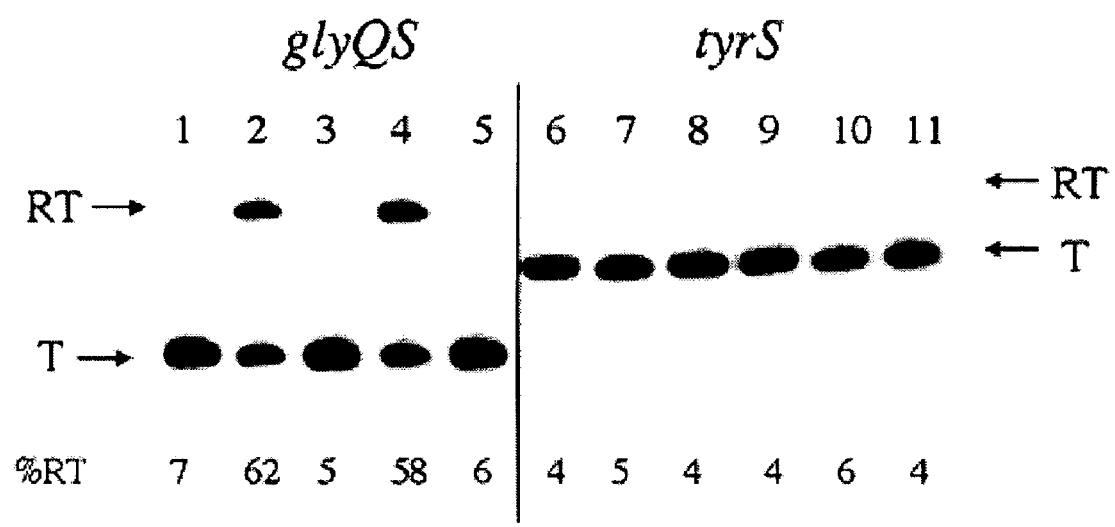

FIG. 9 shows results of in vitro transcription of the glyQS and tyrS leader regions. Lanes 1-5, glyQS DNA; lanes 6-11, tyrS DNA. Lanes 1, 3, and 6, no tRNA added; lanes 2, 4, and 7, tRNA$^{Gly}$ (T7 transcript); lanes 5, 8, and 11, tRNA$^{Tyr}$ (T7 transcript); lane 9, *E. coli* tRNA$^{Tyr}$ (modified, purchased from Sigma); lanes 3-9, NusA added; lanes 1, 2, 10, and 11, no NusA. T=terminated transcript; RT=read-through transcript. Percent read-through is indicated at the bottom of each lane.

Figure 10:
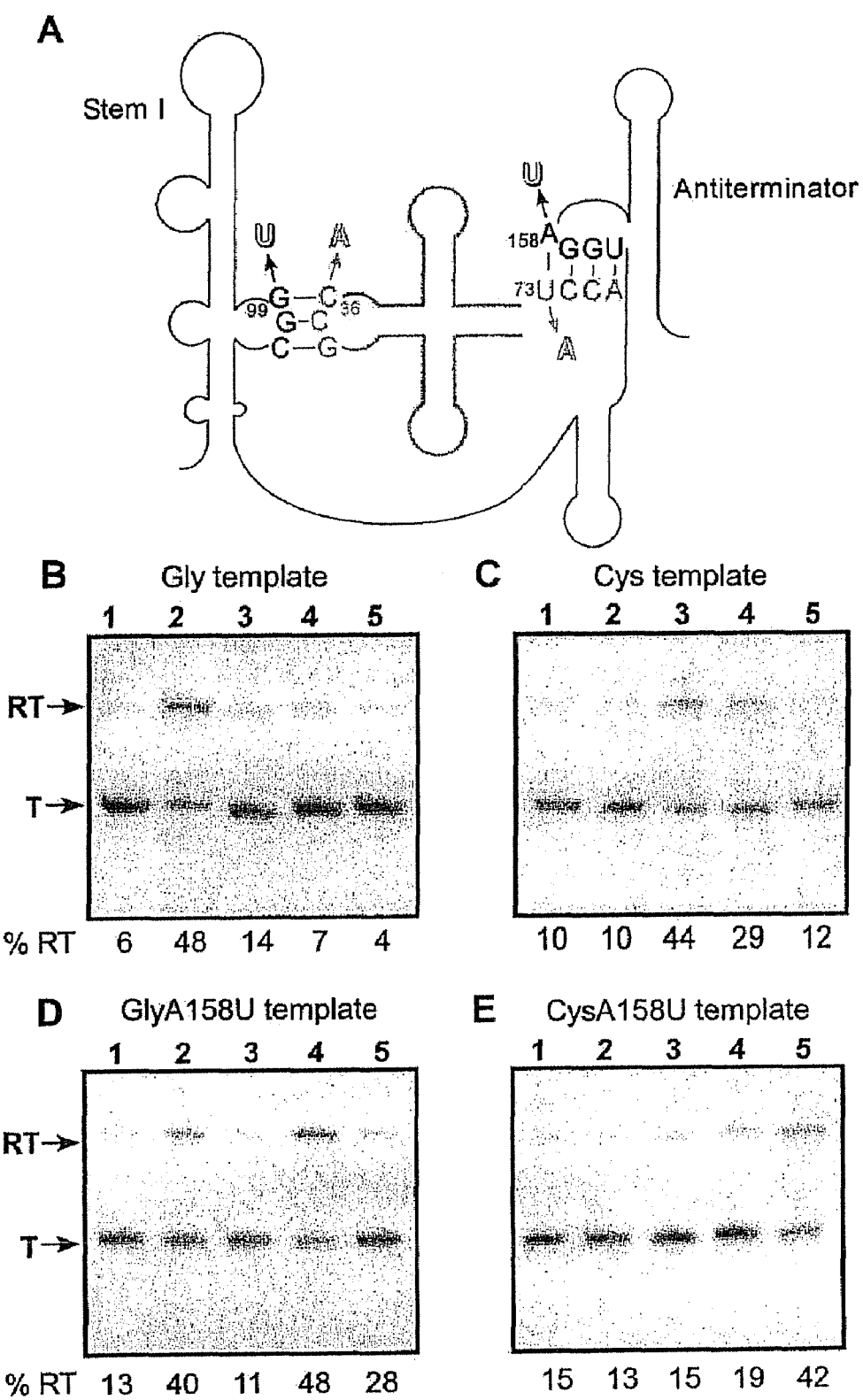

FIG. 10 shows specificity of the glyQS-tRNA$^{Gly}$ interaction. (A) Interaction of the glyQS leader in the antiterminator conformation with tRNA$^{Gly}$. Substitutions at the specifier sequence and antiterminator regions of the leader, and at the anticodon and acceptor end of the tRNA, are shown with arrows. (B-E) show in vitro transcription reactions using different combinations of variants of glyQS templates and tRNA$^{Gly}$. (B) Wild-type glyQS template DNA (GGC specifier sequence, A158 antiterminator). (C) glyQS-UGC template DNA (cysteine specifier sequence, A158 antiterminator). (D) glyQS-A1583U template DNA (GGC specifier, U158 antiterminator). (E) glyQS-UGC/A1583U template DNA (cysteine specifier sequence, U158 antiterminator). Lane 1, no tRNA; lane 2, wild-type tRNA$^{Gly}$ (GCC anticodon, U73 discriminator); lane 3, tRNA$^{Gly}$-GCA (GCA anticodon, U73 discriminator); lane 4, tRNA$^{Gly}$-U733A (GCC anticodon, A73 discriminator); lane 5, tRNA$^{Gly}$-GCA/U733A(GCA anticodon, A73 discriminator). T, terminated transcript; RT, read-through transcript. Percent read-through is indicated at the bottom of each lane.

FIG. 11 shows the polynucleotide sequence for the glyQS gene from *Bacillus subtilis* corresponding to the in vitro transcription template (SEQ ID NO: 21): from *B. subtilis* 168 (obtained from SubtiList Web site).

FIG. 12 shows the polynucleotide sequence for the glyQS DNA template from *Bacillus subtilis* strain BR151MA (SEQ ID NO: 22), a 440 nucleotide fragment that corresponds to the gene sequence from 135 nucleotides upstream of the glyQS transcription start site to nucleotide position 305 of the transcript; the termination site is predicted to be around position 220.

FIG. 13 shows the tRNA$^{Gly}$ DNA sequence (SEQ ID NO: 23): (from SubtiList, confirmed by sequencing of this region in BR151MA).

FIG. 14 shows the PCR primers used for preparing glyQS and tyrS templates for in vitro transcription (SEQ ID NOS 24-27, respectively in order of appearance):

FIG. 15 shows the polynucleotide sequence for the tyrS template sequence (SEQ ID NO: 28) (for strain 168 per SubtiList website and confirmed for strain BR151MA).

FIG. 16 shows the polynucleotide sequences for the oligonucleotide primers (SEQ ID NOS 29-36, respectively in order of appearance) used to generate the tRNA$^{Gly}$ and tRNA$^{Tyr}$.

FIG. 17 shows the tRNA$^{Tyr}$ DNA sequence (SEQ ID NO: 37) (from SubtiList, confirmed by sequencing of this region in BR151MA).

DETAILED DESCRIPTION

The present invention relates to a new assay procedure and system for identifying substances which inhibit the transcription of aminoacyl-tRNA synthetases, particularly in Gram-positive bacteria. The assay can be used to screen for inhibitors that specifically inhibit the T-box antitermination mechanism. Such substances would be useful as antimicrobials, such as, for example, antibiotics.

Definitions

"Antitermination," as used herein, refers to the mechanism by which a T-box termination/antitermination complex is affected to permit read-through of the terminator sequence on the nascent mRNA, and thus permit full transcription of the encoded mRNA.

"Antiterminator," as used herein, refers to the sequence in the nascent mRNA (and its complimentary DNA) that functions in the T-box termination/antitermination complex to permit read-through of the terminator sequence on the nascent mRNA, and thus permit full transcription of the encoded mRNA.

"Divalent metal cation," as used herein, refers to the species of metal cations that are useful components of in vitro transcription assay systems, and include magnesium ($Mg^{2+}$).

"Effector," as used herein, refers to a transcription component, such as a tRNA, which affects or actuates the T-box terminator/antiterminator complex.

"glyQS," as used herein, refers to either a DNA molecule which comprises all or a portion of a bacterial glyQS gene, including the promoter and leader regions, and optionally all or a portion of the polynucleotide coding sequence encoding a wild-type or variant bacterial glycyl-tRNA synthetase, or an mRNA product encoded by the same.

"Gram positive bacteria," as used herein, means the phylogenetic group of bacteria commonly known as and referred to as the Gram-positive branch.

"Leader," as used herein, refers to a wild-type or variant form of the upstream portion of a bacterial gene, particularly a bacterial gene which is regulated by a T-box termination/antitermination complex, and which comprises the elements of a T-box termination/antitermination complex, including a specifier sequence, a T-box, and conserved terminator and antiterminator consensus motifs. Variants comprise modifications to one or both of the specifier and T-box sequences, wherein modifications to either are made to alter the specificity for a cognate tRNA such that the modified specifier and T-box sequences recognize a different tRNA than is recognized by the wild-type specifier and T-box sequences.

"Halted-complex transcription assay system," as used herein, refers to an in vitro transcription assay system in which one of the four nucleoside triphosphates required for complete RNA synthesis is excluded from the initial incubation conditions, resulting in the temporary stalling of the RNA polymerase transcriptional complex at a particular location on the template DNA; in the case of transcription of glyQS, omission of CTP (cytosine triphsophate) results in an arrest in transcription prior to incorporation of the residue at position +17 (the first cytosine residue in the glyQS nascent RNA encoded by the template DNA). The halted-complex system is useful to permit transcription initiation and transcription elongation to be carried out under different conditions or with different reaction components. Transcription is initiated under a first set of conditions in the absence of one of the four NTPs; subsequently, transcription elongation is carried out under a second set of conditions upon the addition of excluded NTP. "Inhibitor," as used herein, refers to a substance which in any way interferes with antitermination so as to effectively block the transcription of a bacterial gene that is regulated by the T-box mechanism, such as a bacterial aminoacyl-tRNA synthetase gene. Substances which are identified using the disclosed screening methods may be used as inhibitors of transcription of such genes to block production of the gene product in bacterial cells. Such inhibitors may thus be useful as antimicrobials. The inhibitors may be added to foodstuffs, or other products such as cosmetics. The inhibitors may be useful for the treatment of plants to prevent the proliferation of infective organisms. The inhibitors may also be useful as treatment or prophylactics in animals, particularly humans. "mRNA read-through product," as used herein, refers to the mRNA product which includes the leader sequence and a portion of mRNA that is downstream from the leader sequence, which is encoded by a template DNA. "Promoter," as used herein, refers to a DNA sequence that allows efficient recognition and transcription initiation by bacterial RNA polymerase (RNAP); examples include the B. subtilis glyQS promoter, and the B. subtilis rpsD promoter, which allow high level transcription (are efficiently recognized by a bacterial RNA polymerase complex). "Read-through," as used herein, refers to the process by which the RNA polymerase transcriptional complex proceeds through the leader sequence to produce an mRNA transcript of the aminoacyl-tRNA synthetase. In the context of the T-box control mechanism, read-through is a result of successful antitermination; read-through does not occur if antitermination is inhibited or otherwise unsuccessful. "Specifier," as used herein, refers to the specific tri-nucleotide sequence in a polynucleotide sequence comprising the upstream untranslated region of a gene encoding a bacterial aminoacyl-tRNA synthetase; the specifier sequence is specific for and interacts with the cognate tRNA anticodon. "Template DNA," as used herein, refers to the polynucleotide used according to the inventions hereof which encodes all or a fragment of a T-box-regulated gene, such as the Bacillus subtilis glycyl-tRNA synthetase gene, and comprises, in order from the 5' to the 3' end: (i) a bacterial promoter; (ii) a leader comprising all or part of a leader, as defined herein, including a transcription initiation site; and (iii) a downstream polynucleotide of sufficient length for detection of a read-through mRNA product, located downstream of the leader region terminator. The downstream portion may vary from 30 to over 100 nucleotide residues, and may be approximately 30 or more nucleotide residues. "Terminator," as used herein, refers to the sequence in the nascent mRNA (and its complimentary DNA) that functions in the T-box termination/antitermination complex to halt transcription of the encoded mRNA. "RNA polymerase" (RNAP), as used herein, refers to an enzyme complex isolated from a bacterial species (either B. subtilis or E. coli have been tested in this system) that is capable of recognizing the promoter region on the test DNA template and exhibits efficient termination at the T box leader terminator during transcription in the absence of tRNA, and efficient tRNA-directed read-through of the leader region terminator when the appropriate tRNA is present in the incubation mixture. "tRNA" as used herein refers to purified RNA generated by in vitro transcription using T7 RNAP, using a template DNA designed so that the transcription product is identical in sequence to tRNA$^{Gly}$.

The T-Box Family of Genes and T-box Transcription Control

Figure 1:
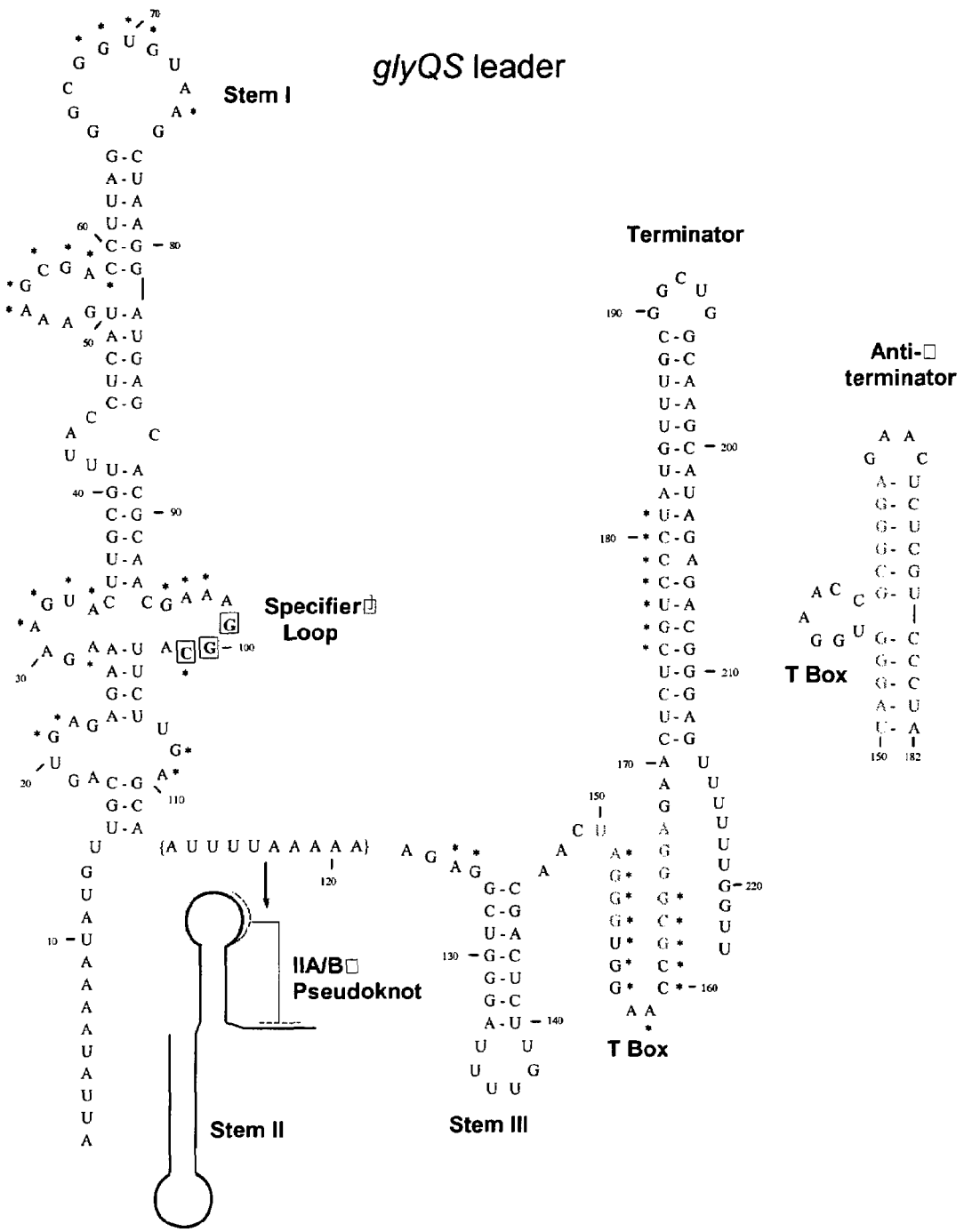
FIG. 1 shows a secondary structure model of the *B. subtilis* glyQS leader RNA encoded by a template DNA (SEQ ID NO: 1). Sequence is shown from the transcription start site (+1) through the end of the leader region terminator; the alternate antiterminator is shown to the right of the terminator (bases 150-182 of SEQ ID NO: 1). The structure is based on the co-variation model of T box family leaders (2, 5). Major conserved features are labeled, and conserved primary sequence elements are denoted with asterisks. The specifier sequence residues are boxed. The glyQS sequence was obtained from the *B. subtilis* genome sequence (11); Sequencing of this region of DNA from strain BR151MA revealed a substitution of A for U at position +6. The residues in brackets (residues 113-122) are replaced by the Stem II and IIA/B elements in most T box family leaders, including *B. subtilis* tyrS.
Figure 2:
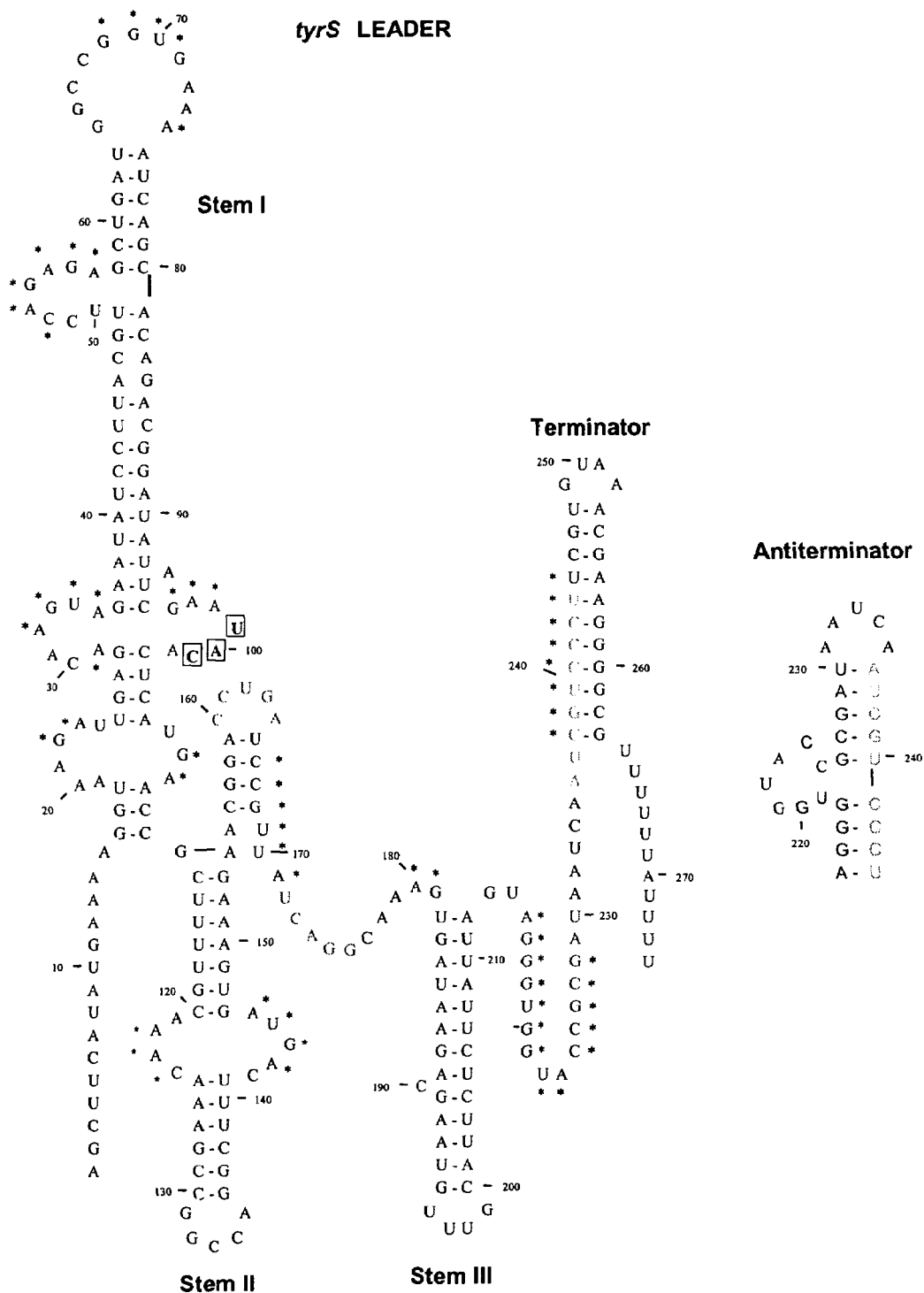
FIG. 2 shows a secondary structure model of the *B. subtilis* tyrS leader RNA (SEQ ID NO: 2). Sequence is shown from the transcription start site through the end of the leader region terminator; the alternate antiterminator is shown to the right of the terminator (bases 215-244 of SEQ ID NO: 2). Major conserved features are labeled, and conserved primary sequence elements are denoted with asterisks. The specifier sequence residues are boxed. The tyrS sequence was obtained from the *B. subtilis* genome sequence (11); the Stem II element is common to most T box family leaders, except glyQS genes.

The T box transcription termination control system is widely used in Gram-positive bacteria to regulate expression of aminoacyl-tRNA synthetase, amino acid biosynthesis, and transporter genes (1). Genes in the T box family contain a set of conserved elements in the leader region of the mRNA. The transcripts of genes regulated by this mechanism contain a 200- to 300-nucleotide un-translated leader that includes a factor-independent (intrinsic) transcription termination signal and a competing antiterminator structure (2). FIGS. 1 and 2, respectively, show secondary structure models of the glyQS and tyrS leaders from *Bacillus subtilis*. FIG. 3 shows the aligned sequences for the glyS leader from sixteen different bacterial strains, as well as the tyrS leader from one bacterial strain. FIG. 4 shows a list of organisms in which T-box family genes have been identified. These include primarily Gram-positive bacteria, as well as some other non-Gram-positive bacterial strains. Not all of these organisms have glyQS under this regulatory system, but all of the organisms listed have at least one gene with a T box leader. Of this group, the most important pathogens are *Bacillus anthracis, Mycobacterium* sp., *Streptococcus* sp., *Staphylococcus* sp., *Clostridium* sp., *Listeria monocytogenes*, and *Enterococcus* sp.

Expression of each gene regulated by the T box termination/antiterminaton complex is dependent on transcription past the leader region termination site; this occurs by stabilization of the antiterminator element by interaction of the leader region of the nascent mRNA of the target gene with a specific class of transfer RNA in the cell. Read-through of the leader region terminator on the nascent mRNA occurs when the charged to uncharged ratio of the corresponding tRNA iso-acceptor is decreased, signaling a deficiency in that aminoacyl-tRNA synthetase or amino acid. (FIG. 5) Sequence comparisons and mutational studies identified a single codon, displayed at a precise position within the leader RNA structure, the "specifier," which determines the specificity of the amino acid response, presumably by pairing with the anticodon of the cognate tRNA (2). As depicted in FIG. 6, the acceptor end of uncharged tRNA apparently makes a second interaction with a bulged region in the antiterminator, based on genetic analyses as well as gel-shift assays using a model 39-nucleotide antiterminator RNA (3, 4); this interaction is proposed to stabilize the antiterminator, preventing the formation of a competing terminator helix (FIG. 7). Mutational studies of the *Bacillus subtilis* tyrS leader and tRNA$^{Tyr}$ have indicated that read-through requires additional conserved features of both RNAs (5-7).

Recognition of the tRNA by the leader RNA may mimic recognition by an aminoacyl-tRNA synthetase, which often exploits the anticodon and discriminator positions as specificity determinants (24). As is also true for tRNA charging, the leader RNA-tRNA interaction in vivo may involve additional determinants (6, 21). Other systems in which uncharged tRNA is monitored, such as the yeast GCN2 system (25), require a protein component; tRNA mimics such as the *E. coli* thrS regulatory target site are also recognized by a protein (26). In translationally coupled transcription attenuation systems such as the *E. coli* trp operon, tRNA charging is monitored by a translating ribosome (27).

It has previously been established that uncharged tRNA is essential for antitermination; however, it was not known whether other factors are also required to mediate the tRNA-leader interaction. The ability of tRNA$^{Tyr}$ mutants to suppress tyrS leader mutations provided strong evidence for the role of uncharged tRNA as the effector for transcription antitermination in the T box system (2, 3). However, it was unknown whether the tRNA acted alone or in conjunction with trans-acting factors required to mediate the leader RNA-tRNA interaction. As disclosed herein, factor- and ribosome-independent antitermination of the *Bacillus subtilis* glyQS leader is dependent on and specific for tRNA$^{Gly}$ and is achieved in a purified in vitro transcription system.

Template DNA Fragments

Template DNA fragments refers to the polynucleotide used according to the inventions hereof which encodes all or a fragment of a T-box-regulated gene and includes a promoter and the T-box leader, and approximately 30 or more nucleotide residues downstream of the leader region terminator. FIG. 8 shows a map of the *Bacillus subtilis* glyQ promoter and leader regions, which indicates the relative positions of the promoter sequence (including the −35 and −10 regions for recognition by RNAP), the transcription initiation site (position +1), the first several residues of the leader (including the location of the first cytosine residue at +17, which corresponds to the halt location in an assay mixture from which the NTP cytosine triphosphate has been excluded). FIG. 1 shows the full leader portion of the *Bacillus subtilis* glyQS, including the specific locations of the specifier and terminator sequences.

A template DNA may include wild-type sequences for the promoter, transcription initiator and leader sequences. Alternatively, one or more of these portions of a template DNA fragment may be a variant of a wild type, or may be a synthetic construct. Specifically, variants of the transcription initiator sequence may be made. For example, according to the present disclosure, variants of the *Bacillus subtilis* glyQS template have been made in which the +2 position (1 nt downstream of the transcription initiation site) is changed from T to C, to allow initiation with the dinucleotide ApC instead of ApU. This is a demonstration that variants of transcription initiator sequence may be used in the assays disclosed herein. Likewise, either or both the specifier and the terminator portions of a wild-type template may be varied to allow the recognition of non-wild type tRNAs. Typically, mutations are introduced into both the specifier and terminator/T-box elements of a leader to alter the specificity of those sequences for tRNA such that the variant forms of the elements recognize a tRNA which is different from that recognized by the wild type specifier and T-box elements. Similarly, the anticodon and discriminator portions of wild type tRNAs may be varied to permit the use of non-wild type tRNAs that will compliment with a wild-type or variant template DNA. Typically, mutations are introduced into both the anticodon and discriminator portions of a tRNA to alter the specificity of those sequences for a leader such that the variant forms of the elements recognize a leader which is different from that recognized by the wild type tRNA anticodon and discriminator. Mutations in leaders and tRNAs may be coordinated such that a wild type leader and its wild type tRNA are both mutated to maintain cognate recognition between the two. Examples are provided herein in the Examples section. Methods for preparing such variants are described herein and are additionally well known in the art.

The portion of the template DNA which is downstream from the terminator of the leader portion is preferably from about 30 to 150 nucleotide residues in length, to allow easy discrimination between the terminated and read-through products in a low resolution polyacrylamide gel electrophoresis system. Read-through products may be measured by alternate methods, e.g., by PCR amplification using an oligonucleotide primer that hybridizes only to the read-through product.

Screening for Inhibitors of Antitermination

Substances which may be inhibitors of bacterial aminoacyl-tRNA synthetase transcription are screened using the disclosed in vitro bacterial transcription assay system. The screening process involves the following steps:

a) incubating in parallel two mixtures, each containing a divalent metal cation, NTPs, a dinucleotide (as dictated by the specific transcription initiator sequence in the template DNA), a template DNA fragment containing a promoter, and the leader region of a bacterial gene which is regulated by the T-box mechanism, such as the *B. subtilis* glyQS gene, which encodes glycyl-tRNA synthetase, a bacterial RNA polymerase complex, and a tRNA, such as tRNA$^{Gly}$ which is capable of appropriate interaction with the leader sequence, wherein one of the NTPs is excluded from the mixture to permit halting of the complex approximately 10-20 nucleotide residues into the nascent mRNA, and b) adding to both mixtures the excluded NTP, and adding to only one of the two mixtures a test agent which is a potential inhibitor substance; and c) comparing the amount of mRNA read-through product produced in the mixture lacking the potential inhibitor with the amount of mRNA read-through product produced in the mixture containing the potential inhibitor. An inhibitor of the antiterminator (i.e., an inhibitor of read-through) will cause a reduction in the amount of mRNA read-through product as compared to the mixture lacking the test agent.

Optionally, the incubation steps (a) and (b) may comprise all four NTPs, in which case, each of the incubations will proceed with transcription elongation immediately following transcription initiation. If the selected NTP is excluded from the initial incubation mixtures, the reactions in each case will be halted at the first encountered residue in the nascent mRNA which codes for the excluded NTP. Preferably, the residue is at residue position 10-50 of the nascent mRNA, and more preferably at residue position 10-20. By excluding a selected NTP which would result in halting within the preferred residue position range, the reactions may be halted for a brief time, by chilling, for example. Thereafter, the conditions may be altered by addition of other factors or agents, and upon return to appropriate incubation conditions and/or addition of the excluded NTP, elongation of transcription will proceed.

Multiple mixtures may be run in parallel, where one or more of the mixtures serve as appropriate controls, and one or more of the mixtures are used to test a variety of test agents or a range of test agent conditions. Likewise, the incubation mixture may be initially prepared as a large single mixture (bulk mixture) which is thereafter aliquoted into two or more separate mixtures for evaluation of control or test conditions or agents. Preferably, the bulk mixture is a halted complex transcription assay system.

EXAMPLES

Example 1

In Vitro Transcription of glyQS mRNA

Bacterial Strains and Growth Conditions. *B. subtilis* strain BR151MA (lys-3 trpC2) was used as the source of chromosomal DNA for amplification by PCR. Strains 1A5 (glyB133 metC3 tre-12 trpC2; Bacillus Genetic Stock Center) and KS115 (cysA14 hisA1 leuA8 metC3 trpC2; K. Sandman, Ohio State Univ., Columbus) were used for amino acid limitation experiments for glycine and cysteine, respectively. Cells were propagated in 2×YT medium (9) or in Spizizen minimal medium (10) for measurements of lacZ fusion expression. Cells containing lacZ fusions were grown in the presence of chloramphenicol at 5 µg/ml.

In Vitro Transcription Assays. The template for glyQS transcription was a 440-bp PCR fragment that included sequences from 135 bp upstream of the glyQS transcription start site to position 305 of the transcript; the termination site is predicted to be around position 220 (ref. 11; FIG. 1; FIG. 12). The template for tyrS transcription was a 420-bp PCR fragment including sequences from 85 bp upstream of the transcription start site to position 335 of the transcript; the termination site is predicted to be around position 270 (ref. 12; FIG. 15). PCR products were purified by a Qiagen PCR cleanup kit. Template DNA (10 nM) was incubated in 1×transcription buffer (13) with His-tagged *B. subtilis* RNA polymerase (RNAP) (6 nM) purified as described by Qi and Hulett (14). Halted complex transcription assays were carried out essentially as described by Landick et al. (15).

The dinucleotide ApU (150 µM, Sigma) was used to initiate glyQS transcription. ATP and GTP were added to 2.5 µM, UTP was added to 0.75 µM, and [alpha-P$^{32}$]UTP (800 Ci/mmol; 1 Ci=37 GBq) was added to 0.25 µM. Transcription of glyQS was initiated in the absence of CTP; for the glyQS gene, the first C is at position +17 so that the transcription elongation complex halts after synthesis of 16 nt under these conditions. The dinucleotide ApG was used for initiation of tyrS transcription, and GTP was omitted from the initiation reaction, resulting in a halt at position +11. The initiation reaction mixtures were incubated at 37° C. for 15 min and were then placed on ice. Heparin (20 µg/ml, Sigma) was added to block re-initiation, and elongation was triggered by the addition of NTPs to 10 µM final and other reagents as indicated. *B. subtilis* NusA protein (25 nM), purified as described previously (13), was included in the elongation reaction as indicated. *Escherichia coli* RNAP, prepared as described (16), was used at 10 nM. Transcription reactions were terminated by extraction with phenol, and the products were resolved by denaturing 6% polyacrylamide gel electrophoresis and visualized by Phosphor-Imager analysis.

Unmodified *B. subtilis* tRNA$^{Gly}$ and tRNA$^{Tyr}$ were made by T7 transcription using a PCR fragment generated with a 5' oligonucleotide primer that included a T7 promoter sequence, positioned so that the first base of the transcript is the first position of the tRNA, and the final position of the PCR product corresponds to 3' position of the tRNA (FIGS. 13, 16, 17). T7 transcription was carried out by using an Ampliscribe T7 transcription kit (Epicentre Technologies, Madison, Wis.). The tRNA transcripts were purified on a 6% denaturing polyacrylamide gel, visualized by using UV shadowing, and eluted into 300 mM NaOAc, pH 4.5/1 mM EDTA. The tRNA was purified by extraction with phenol, precipitated with ethanol, and suspended in water. The resulting tRNA was refolded by incubation at 80° C. for 2 min and slow cooling to room temperature before use in the transcription assays at 70 nM. Modified *E. coli* tRNA$^{Tyr}$ was purchased from Sigma.

Mutations in the glyQS template DNA and tRNA$^{Gly}$ (as shown in FIG. 10A) were introduced by PCR, using oligonucleotide primers containing the desired alterations.

Example 2

Ex Vivo Expression of Aminoacyl-glyQS-synthetase mRNA

β-Galactosidase Measurements. The glyQS DNA fragment used for in vitro transcription, as described in EXAMPLE 1, was inserted into the lacZ fusion vector pFG328 (17) and integrated in single copy into the *B. subtilis* chromosome by recombination into a bacteriophage SPbeta prophage. Cells were grown in minimal medium containing all required amino acids at 50 µg/ml until mid-exponential growth phase and were then collected and divided into two cultures, containing all required amino acids or with one amino acid at 5 µg/ml. Growth was continued for 4 h, and cells were harvested and assayed for β-galactosidase activity, expressed as Miller units (9). Glycine starvation experiments were carried out in strain 1A5 (Gly-), and cysteine starvation experiments were carried out in strain KS 115 (Cys-). All samples were assayed in duplicate, and growth experiments were carried out at least twice; variation was <10%.

Example 3

In Vitro tRNA-Directed Antitermination of glyQS-aminoacyl-tRNA Synthetase mRNA Transcription In the presence of 30 mM $MgCl_2$ and low NTP concentrations (10 μM) during the elongation reaction, the glyQS leader region terminator was highly efficient (FIG. 9). Addition of a T7 RNAP-generated transcript of *B. subtilis* $tRNA^{Gly}$ dramatically increased read-through from 5% (lane 1 or 3) to approximately 60% (lane 2 or 4), with a corresponding decrease in the amount of the terminated transcript. No tRNA-dependent read-through was observed at lower $MgCl_2$ concentrations or at higher NTP concentrations (data not shown). $Mg^{2+}$ plays a crucial role in RNA folding reactions (19) and may facilitate folding of the nascent transcript into the correct conformation for interaction with the tRNA and antitermination. The rate of transcription elongation is decreased at low NTP concentrations (20), which may favor formation of the correct RNA structure or facilitate pausing by RNAP.

Antitermination of the glyQS leader responded specifically to $tRNA^{Gly}$; addition of $tRNA^{Tyr}$ had no effect (FIG. 9, lane 5). Neither $tRNA^{Gly}$ nor $tRNA^{Tyr}$ addition increased read-through of the *B. subtilis* tyrS leader region terminator (FIG. 9, lanes 6-11). Therefore, either the tyrS and glyQS leaders have different requirements for the tRNA-leader interaction or the tyrS leader fails to fold properly under the in vitro conditions used. The Stem II and Stem IIA/B pseudoknot elements present in tyrS but absent in glyQS may be responsible for this difference. Single nucleotide substitutions that disrupt conserved elements of the Stem IIA/B region in the tyrS leader result in loss of read-through in vivo, indicating that this region is functionally required in the tyrS context (5). A variant of the tyrS leader in which the specifier sequence and antiterminator were changed to match the anticodon and acceptor end of $tRNA^{Gly}$ has been constructed, and expression was shown to be induced in vivo in response to limitation for glycine (21). This leader variant failed to respond to $tRNA^{Gly}$ in vitro (data not shown), indicating that the codon-anticodon interaction (GGC.GCC for glyQS vs. UAC.GUA for tyrS) is not sufficient to explain the lack of $tRNA^{Tyr}$-directed antitermination of the tyrS leader in vitro.

Example 4 glyQS Antitermination In Vitro is Independent of NusA and Functions with *E. coli* RNAP The NusA protein affects transcription elongation rates and sensitivity of RNAP to pause and termination sites, and participates in a number of transcription termination control systems, including phage lambda N and Q antitermination (22). Addition of *B. subtilis* NusA to the glyQS antitermination reaction resulted in a small increase in termination in the absence of tRNA, especially at high NTP concentrations (ref. 13; data not shown). However, the $tRNA^{Gly}$-dependent increase in read-through occurred both in the presence and absence of NusA (compare FIG. 9, lanes 1 and 2 with lanes 3 and 4), indicating that NusA is not required for glyQS antitermination under these conditions.

The ability of *E. coli* RNAP to replace *B. subtilis* RNAP in the tRNA-dependent transcription antitermination assay was tested to determine whether this activity was sensitive to the source of RNAP. RNAP from *E. coli* and *B. subtilis* has been shown to exhibit different patterns of recognition of pausing and termination signals (ref. 23; unpublished results). *E. coli* RNAP exhibited $tRNA^{Gly}$-dependent read-through similar to that observed with *B. subtilis* RNAP (data not shown), indicating that the antitermination event is dependent on features of the transcript, but not on the enzyme that generates the transcript. Introduction of T box leaders, including glyQS, into *E. coli*, from which this antitermination system is absent, generally resulted in a high level of read-through of the leader region terminator independent of amino acid limitation (data not shown), suggesting that the leader region terminators function poorly in the heterologous host and that the proper leader-tRNA interaction does not occur.

Example 5

Characterization of Specificity Determinants for Antitermination In Vitro and In Vivo The specificity of the tRNA effect was further tested by using glyQS leader variants and corresponding $tRNA^{Gly}$ variants (FIG. 10A). The GGC glycine specifier sequence was changed to a UGC cysteine codon, and position A158 of the glyQS antiterminator bulge was changed to a U; this position is a secondary determinant of the specificity of the tRNA-leader interaction (3). The mutations were tested separately and in combination, both in vitro and in vivo. The wild-type glyQS template exhibited efficient antitermination in vitro only in combination with the corresponding wild-type $tRNA^{Gly}$ (FIG. 10B, lane 2). The UGC specifier mutation in the glyQS leader resulted in decreased antitermination by wild-type $tRNA^{Gly}$; this effect was suppressed by a variant of $tRNA^{Gly}$ with an anticodon complementary to UGC (FIG. 10C, lane 3). The A1583U substitution in the antiterminator also decreased antitermination directed by wild-type $tRNA^{Gly}$ and was suppressed by a corresponding change in the tRNA discriminator base (FIG. 10D, lane 4). The specificity pattern also held for the UGC/A1583U double mutant, with the most efficient antitermination occurring in response to the matching tRNA (FIG. 10E, lane 5). The native GGC.GCC codon-anticodon pairing consistently resulted in more efficient antitermination than the UGC.GCA cysteinyl combination; this could be due to the extra G.C pair or to other features of the glyQS leader that are adapted to the native glycyl combination.

In agreement with the in vitro results, a wild-type glyQS-lacZ transcriptional fusion exhibited induction in vivo in response to limitation for glycine, but it failed to respond to limitation for cysteine (Table 1). Replacement of the GGC glycine specifier sequence with a UGC cysteine codon resulted in loss of the response to glycine and induction in response to limitation for cysteine; both $tRNA^{Gly}$ and $tRNA^{Cys}$ contain a U at the discriminator position. The A1583U mutation, either alone or in combination with the UGC cysteine specifier sequence mutation, abolished the response to either glycine or cysteine, consistent with the loss of a match with the U discriminator position. The maximum expression observed under glycine limitation conditions was approximately one-third of that observed in a construct from which the terminator was deleted, indicating that full induction was not observed under these conditions.

TABLE 1

Expression of glyQS-lacZ fusions in vivo. Expression was measured by activity of β-galactosidase, in Miller units (9). ND, not determined; ΔTerm, terminator deleted.

| Fusion | Glycine Starvation | | | Cysteine Starvation | | |
|---|---|---|---|---|---|---|
| | +Glycine | −Glycine | Ratio | +Cysteine | −Cysteine | Ratio |
| GGC-A158 | 42 | 130 | 3.1 | 34 | 29 | 0.85 |
| UGC-A158 | 58 | 42 | 0.72 | 31 | 90 | 2.9 |
| GGC-U158 | 24 | 11 | 0.45 | ND | ND | ND |
| UGC-U158 | 20 | 6.0 | 0.30 | 14 | 9.1 | 0.65 |
| ΔTerm | 350 | 360 | 1.0 | ND | ND | ND |

REFERENCES

1. Henkin, T. M. (2000) *Curr. Opin. Microbiol.* 3, 149-153.
2. Grundy, F. J. & Henkin, T. M. (1993) *Cell* 74, 475-482.
3. Grundy, F. J., Rollins, S. M. & Henkin, T. M. (1994) *J. Bacteriol.* 176, 4518-4526.
4. Gerdeman, M. S., Henkin, T. M. & Hines, J. V. (2002) *Nucleic Acids Res.* 30, 1065-1072.
5. Rollins, S. M., Grundy, F. J. & Henkin, T. M. (1997) *Mol. Microbiol.* 25, 411-421.
6. Grundy, F. J., Collins, J. A., Rollins, S. M. & Henkin, T. M. (2000) *RNA* 6, 1131-1141.
7. Winkler, W. C., Grundy, F. J., Murphy, B. A. & Henkin, T. M. (2001) *RNA* 7, 1165-1172.
8. Grandoni, J. A., Fulmer, S. B., Brizzio, V., Zahler, S. A. & Calvo, J. M. (1993) *J. Bacteriol.* 175, 7581-7593.
9. Miller, J. H. (1972) *Experiments in Molecular Genetics* (Cold Spring Harbor Lab. Press, Plainview, N.Y.).
10. Anagnostopoulos, C. & Spizizen, J. (1961) *J. Bacteriol.* 81, 741-746.
11. Kunst, F., Ogasawara, N., Moszer, I., Albertini, A. M., Alloni, G., Azevedo, V., Bertero, M. G., Bessieres, P., Bolotin, A., Borchert, S., Borriss, R., et al. (1997) *Nature (London)* 390, 249-256.
12. Henkin, T. M., Glass, B. L. & Grundy, F. J. (1992) *J. Bacteriol.* 174, 1299-1306.
13. Grundy, F. J., Moir, T. R., Haldeman, M. T. & Henkin, T. M. (2002) *Nucleic Acids Res.* 30, 1646-1655.
14. Qi, Y. & Hulett, F. M. (1998) *Mol. Microbiol.* 28, 1187-1197.
15. Landick, R., Wang, D. & Chan, C. L. (1996) *Methods Enzymol.* 274, 334-353.
16. Hager, D. A., Jin, D. J. & Burgess, R. R. (1990) *Biochemistry* 29, 7890-7894.
17. Grundy, F. J., Waters, D. A., Allen, S. H. G.&Henkin, T. M. (1993) *J. Bacteriol.* 175, 7348-7355.
18. Luo, D., Condon, C., Grunberg-Manago, M. & Putzer, H. (1998) *Nucleic Acids Res.* 26, 5379-5387.
19. Treiber, D. K. & Williamson, J. R. (2001) *Curr. Opin. Struct. Biol.* 11, 309-314.
20. Rhodes, G. & Chamberlin, M. J. (1974) *J. Biol. Chem.* 249, 6675-6683.
21. Grundy, F. J., Hodil, S. E., Rollins, S. M. & Henkin, T. M. (1997) *J. Bacteriol.* 179, 2587-2594.
22. Friedman, D. I. & Court, D. L. (2001) *Curr. Opin. Microbiol.* 4, 201-207.
23. Artsimovitch, I., Svetlov, V., Anthony, L., Burgess, R. R. & Landick, R. (2000) *J. Bacteriol.* 182, 6027-6035.
24. Giege, R., Sissler, M. & Florentz, C. (1998) *Nucleic Acids Res.* 26, 5017-5035.
25. Qiu, H., Dong, J., Hu, C., Francklyn, C. S. & Hinnebusch, A. G. (2001) *EMBO J.* 20, 1425-1438.
26. Sankaranarayanan, R., Dock-Bregeon, A.-C., Romby, P., Caillet, J., Springer, M., Rees, B., Ehresmann, C., Ehresmann, B. & Moras, D. (1999) *Cell* 97, 371-381.
27. Landick, R., Turnbough, C. L., Jr., & Yanofsky, C. (1996) in *Escherichia coli and Salmonella: Cellular and Molecular Biology*, eds. Neidhardt, F. C., Curtis, R., III, Ingraham, J. L., Lin, E. C. C., Low, K. B., Magasanik, B., Reznikoff, W. S., Riley, M., Schaecter, A. & Umbarger, H. E. (Am. Soc. Microbiol., Washington, D.C.), pp. 1263-1286.
28. Ban, N., Nissen, P., Hansen, J., Moore, P. B. & Steitz, T. A. (2000) *Science* 289, 905-920.
29. Ogle, J. M., Brodersen, D. E., Clemons, W. M., Jr., Tarry, M. J., Carter, A. P. & Ramakrishnan, V. (2001) *Science* 292, 897-902.
30. Guerrier-Takada, C., Gardiner, K., Marsh, T., Pace, N. & Altman, S. (1983) *Cell* 35, 849-857.
31. Weeks, K. M. & Cech, T. R. (1995) *Cell* 82, 221-230.

The invention claimed is:

1. A method for screening substances which are potential inhibitors of expression of bacterial T-box regulated genes, comprising the steps of:

a) incubating one or more assay mixtures to produce a readthrough mRNA product, wherein the assay mixtures comprise: a template DNA that comprises: (i) a bacterial promoter, (ii) a glyQS leader, including a transcription start site, and (iii) a downstream polynucleotide of sufficient length for detection of a read-through mRNA product; divalent magnesium cations; nucleoside triphosphates; dinucleotides corresponding to and encoded by the transcription start site of the glyQS leader; bacterial RNA polymerase complex; and uncharged tRNA specific for a specifier sequence located in the glyQS leader; and b) incubating a potential inhibitor substance with one or more assay mixtures to produce a readthrough mRNA product, wherein the assay mixtures comprise: a template DNA that comprises: (i) a bacterial promoter, (ii) a glyQS leader, including a transcription start site, and (iii) a downstream polynucleotide of sufficient length for detection of a read-through mRNA product; divalent magnesium cations; nucleoside triphosphates; dinucleotides corresponding to and encoded by the transcription start site of the glyQS leader; bacterial RNA polymerase complex; and uncharged tRNA specific for a specifier sequence located in the glyQS leader;

c) comparing the fraction of total mRNA products corresponding to the read-through mRNA product produced in step a) with the fraction of total mRNA products corresponding to the read-through mRNA product produced in step b)

wherein a lesser fraction of the read-through mRNA product produced in step b) in comparison with step a) indicates that said potential inhibitor substance inhibits transcriptional readthrough of said glyQS leader and therefore is an inhibitor of expression of bacterial T-box regulated genes.

2. The method recited in claim 1 wherein the divalent magnesium cation concentration is about 30 mM.

3. The method recited in claim 1 wherein the nucleoside triphosphates are selected from the group consisting of adenosine triphosphate, guanosine triphosphate, cytosine triphosphate, and uridine triphosphate, and any combination of one or more of these.

4. The method recited in claim 1 wherein the dinucleotides are selected from the group consisting of ApA, ApC, ApU, ApG, GpA, GpC, GpU, GpG, CpA, CpC, CpU, CpG, UpA, UpC, UpU, and UpG.

5. The method recited in claim 1 wherein the bacterial promoter is selected from the group consisting of a *B. subtilis* glyQS promoter and a *B. subtilis* rpsD promoter.

6. The method recited in claim 1 wherein the downstream polynucleotide of sufficient length for detection of a read-through mRNA product comprises a polynucleotide which is from about 30 to 150 nucleotide residues in length.

7. The method recited in claim 1 wherein the uncharged tRNA specific for a specifier sequence located in the glyQS leader is *B. subtilis* tRNA$^{Gly}$.

8. The method recited in claim 1 wherein the RNA polymerase is purified from either *B. subtilis* or *Escherichia coli*.

9. The method recited in claim 1 wherein the glyQS leader comprises a variant glyQS leader sequence which is a variant of a wild-type glyQS leader from a Gram positive bacterial strain, wherein the variant glyQS leader sequence comprises modifications to one or both glyQS leader specifier and antiterminator sequences as compared to the wild-type glyQS leader.

10. The method recited in claim 1 wherein the uncharged tRNA specific for a specifier sequence located in the glyQS leader is a variant of a wild-type tRNA in which either or both wild-type anticodon sequence, or wild-type discriminator sequence, are altered to complement the glyQS leader sequence.

11. The method recited in claim 1 wherein the glyQS leader comprises a variant glyQS leader sequence which is a variant of a wild-type glyQS leader from a Gram positive bacterial strain, wherein the variant glyQS leader sequence comprises modifications to one or both wild-type glyQS leader specifier and antiterminator sequences, and wherein the uncharged tRNA specific for a specifier sequence located in the glyQS leader is a variant of a wild-type tRNA in which either or both wild-type anticodon sequence, or wild-type discriminator sequence are altered to complement the variant glyQS leader sequence.

12. The method recited in claim 1 wherein the assay mixtures comprises an in vitro halted-complex bacterial transcription assay systems.

13. A method for identifying inhibitors of expression of bacterial T-box regulated genes, comprising:
providing two or more in vitro halted-complex bacterial transcription assay systems which comprise a template DNA comprising: (i) a bacterial promoter, (ii) a polynucleotide comprising a portion of a leader from *B. subtilis* glyQS gene and including a transcription start site, and (iii) a downstream polynucleotide of sufficient length for detection of a read-through mRNA product; RNA polymerase, and uncharged *B. subtilis* tRNA$^{Gly}$, wherein at least one or more of said assay systems comprises a test substance, and wherein at least one or more of said assay systems lacks a test substance, and comparing the fraction of total mRNA products corresponding to *B. subtilis* glyQS read-through mRNA produced in each of said assay systems, wherein a test substance is considered an inhibitor if it effects a lesser fraction of total mRNA products corresponding to the *B. subtilis* glyQS read-through mRNA produced in an assay system comprising said test substance as compared to an assay system lacking said test substance.

14. The method recited in claim 13 wherein the bacterial promoter is selected from the group consisting of a *B. subtilis* glyQS promoter and a *B. subtilis* rpsD promoter.

15. The method recited in claim 13 wherein the RNA polymerase is purified from either *B. subtilis* or *Escherichia coli*.

16. The method recited in claim 13 wherein the polynucleotide comprising a portion of the leader from the *B. subtilis* glyQS gene comprises a variant *B. subtilis* glyQS leader sequence comprising modifications to one or both *B. subtilis* glyQS leader specifier and antiterminator sequences as compared to the wild-type glyQS leader, and
wherein the uncharged *B. subtilis* tRNA$^{Gly}$ is a variant of a wild-type *B. subtilis* tRNA$^{Gly}$ in which either or both wild-type anticodon sequence and wild-type discriminator sequence are altered to complement the variant *B. subtilis* glyQS leader sequence.

17. A purified in vitro assay system for screening substances which are potential inhibitors of expression of bacterial T-box regulated genes, comprising:
  a) one or more assay mixtures comprising: a template DNA that comprises: (i) a bacterial promoter, (ii) a glyQS leader, including a transcription start site, and (iii) a downstream polynucleotide of sufficient length for detection of a read-through mRNA product; divalent magnesium cations; nucleoside triphosphates; dinucleotides corresponding to and encoded by the transcription start site of the glyQS leader; bacterial RNA polymerase complex; and uncharged tRNA specific for a specifier sequence located in the glyQS leader; and
  b) one or more assay mixtures comprising: a potential inhibitor substance; a template DNA that comprises: (i) a bacterial promoter, (ii) a glyQS leader, including a transcription start site, and (iii) a downstream polynucleotide of sufficient length for detection of a read-through mRNA product; divalent magnesium cations; nucleoside triphosphates; dinucleotides corresponding to and encoded by the transcription start site of the glyQS leader; bacterial RNA polymerase complex; and uncharged tRNA specific for a specifier sequence located in the glyQS leader.

18. The assay system recited in claim 17 wherein the divalent magnesium cation concentration is about 30 mM.

19. The assay system recited in claim 17 wherein the nucleoside triphosphates are selected from the group consisting of adenosine triphosphate, guanosine triphosphate, cytosine triphosphate, and uridine triphosphate, and any combination of one or more of these.

20. The assay system recited in claim 17 wherein the dinucleotides are selected from the group consisting of ApA, ApC, ApU, ApG, GpA, GpC, GpU, GpG, CpA, CpC, CpU, CpG, UpA, UpC, UpU, and UpG.

21. The assay system recited in claim 17 wherein the bacterial promoter is selected from the group consisting of a *B. subtilis* glyQS promoter and a *B. subtilis* rpsD promoter.

22. The assay system recited in claim 17 wherein the downstream polynucleotide of sufficient length for detection of a read-through mRNA product comprises a polynucleotide which is from about 30 to 150 nucleotide residues in length.

23. The assay system recited in claim 17 wherein the uncharged tRNA specific for a specifier sequence located in the glyQS leader is *B. subtilis* tRNA$^{Gly}$.

24. The assay system recited in claim 17 wherein the RNA polymerase is purified from either *B. subtilis* or *Escherichia coli*.

25. The assay system recited in claim 17 wherein the glyQS leader comprises a variant glyQS leader sequence which is a variant of a wild-type glyQS leader from a Gram positive bacterial strain, wherein the variant glyQS leader sequence comprises modifications to one or both glyQS leader specifier and antiterminator sequences as compared to the wild-type glyQS leader.

26. The assay system recited in claim 17 wherein the uncharged tRNA specific for a specifier located in the glyQS leader is a variant of a wild-type tRNA in which either or both wild-type anticodon sequence, or wild-type discriminator sequence, are altered to complement the glyQS leader sequence.

27. The assay system recited in claim 17 wherein the leader comprises a variant glyQS leader sequence which is a variant of a wild-type glyQS leader from a Gram positive bacterial strain, wherein the variant glyQS leader sequence comprises modifications to one or both glyQS leader specifier antiterminator sequences as compared to the wild-type glyQS leader, and wherein the uncharged tRNA specific for a specifier sequence located in the glyQS leader is a variant of a wild-type tRNA in which either or both wild-type anticodon sequence, or wild-type discriminator sequence are altered to complement the variant glyQS leader sequence.

28. The assay system recited in claim 17 wherein the assay comprises an in vitro halted-complex bacterial transcription assay system.

29. A purified in vitro assay system for identifying inhibitors of expression of bacterial T-box regulated genes, comprising:

two or more in vitro halted-complex bacterial transcription assay systems which comprise a template DNA comprising: (i) a bacterial promoter, (ii) a polynucleotide comprising a portion of a leader from *B. subtilis* glyQS gene, including a transcription start site, and (iii) a downstream polynucleotide of sufficient length for detection of a read-through mRNA product; RNA polymerase, and uncharged *B. subtilis* tRNA$^{Gly}$, wherein at least one or more of said assay systems comprises a test substance, and wherein at least one or more of said assay systems lacks a test substance.

30. The assay system recited in claim 29 wherein the bacterial promoter is selected from the group consisting of a *B. subtilis* glyQS promoter and a *B. subtilis* rpsD promoter.

31. The assay system recited in claim 29 wherein the RNA polymerase is purified from either *B. subtilis* or *Escherichia coli*.

32. The assay system recited in claim 29 wherein the polynucleotide comprising a portion of the leader from the *B. subtilis* glyQS gene comprises a variant *B. subtilis* glyQS leader sequence comprising modifications to one or both *B. subtilis* glyQS leader specifier and antiterminator sequences as compared to the wild-type glyQS leader, and wherein the uncharged *B. subtilis* tRNA$^{Gly}$ is a variant of a wild-type *B. subtilis* tRNA$^{Gly}$ in which either or both wild-type anticodon sequence and wild-type discriminator sequence are altered to complement the variant *B. subtilis* glyQS leader sequence.

* * * * *

SEQUENCE LISTING

<160> NUMBER OF SEQ ID NOS: 37

<210> SEQ ID NO 1
<211> LENGTH: 223
<212> TYPE: RNA
<213> ORGANISM: Bacillus subtilis

<400> SEQUENCE: 1

```
auuauaaaau auguugcagu gagagaaaga aguacuugcg uuuaccucau gaaagcgacc      60
uuagggcggu guaagcuaag gaugagcacg caacgaaagg cauucuugag caauuuuaaa    120
aaagaggcug ggauuuuguu cucagcaacu agguggaac cgcgggagaa cucucguccc     180
uauguuugcg gcuggcaagc auagagacgg gaguuuuuug guu                      223
```

<210> SEQ ID NO 2
<211> LENGTH: 274
<212> TYPE: RNA

```
<213> ORGANISM: Bacillus subtilis

<400> SEQUENCE: 2
agcuucauau gaaagguaa agauugagac aaguagaaua uccuuacguu ccagagagcu      60
gauggccggu gaaaucagc acagacggau auaucgaaua cacucaugaa ccgcuuuugc     120
aaacaaagcc ggccaggcuu ucaguaguga agaacggac cugauccguu aucaggcaaa     180
gugauaagac gaauguuugc auucucuuau uaguagggug guaccgcgau aaucaaucgu     240
cccuucgugu aaacgaaggg gcguuuuuua uuuu                                274

<210> SEQ ID NO 3
<211> LENGTH: 243
<212> TYPE: DNA
<213> ORGANISM: Bacillus subtilis

<400> SEQUENCE: 3
agcttcatat gaaaggtaa agattgagac aagtagaata tccttacgtt ccagagagct      60
gatggccggt gaaatcagc acagacggat atatcgaata cactcatgaa ccgcttttgc     120
aaacaaagcc ggccaggctt tcagtagtga agaacggac ctgatccgtt atcaggaaag     180
tgataagacg aatgtttgca ttctcttatt agtagggtgg taccgcgata atcaatcgtc     240
cct                                                                 243

<210> SEQ ID NO 4
<211> LENGTH: 174
<212> TYPE: DNA
<213> ORGANISM: Bacillus anthracis

<400> SEQUENCE: 4
attattaata taagtagcga tgacggactt ataagtactt gcacaaaaag cgattcaggg      60
atagtgaaag cctgaagccg caaggaaacg gcagtctcga gcaatacgtg ataaagtgga    120
tgcacctttt gtgtatcaac tagggtggaa ccgcgggcaa acgctcgtcc ctag          174

<210> SEQ ID NO 5
<211> LENGTH: 174
<212> TYPE: DNA
<213> ORGANISM: Bacillus cereus

<400> SEQUENCE: 5
attattaata taagtagcga tgacggactt ataagtactt gcacaaaaag cgattcaggg      60
atagtgaaag cctgaagccg caaggaaacg gcagtctcga gcaatacgtg ataaagtgga    120
tgcacctttt gtgtatcaac tagggtggaa ccgcgggcaa acgctcgtcc ctag          174

<210> SEQ ID NO 6
<211> LENGTH: 192
<212> TYPE: DNA
<213> ORGANISM: Bacillus halodurans

<400> SEQUENCE: 6
aatgttatat ttcaatgcta tgacggagaa cagtacttga ttccttttac ataaaagcga      60
acctaggatg gtgagagcta gggatgtaaa catcaaggaa ggcactcttg agcatgaacg    120
atgaaaagaa agtggcctat ggtgtcatca taggcaaata gggtggaacc gcgggttaac    180
tctcgtccct at                                                       192

<210> SEQ ID NO 7
<211> LENGTH: 189
```

```
<212> TYPE: DNA
<213> ORGANISM: Bacillus stearothermophilus

<400> SEQUENCE: 7
aaatcatata tggatcgcga tgacggatca atagtagtta accctctctt cccaagcgag        60
ccggggacgg tggaagcccg gcgaagatgg ttaatgaaac ggcagtccgg agcggaaatg       120
gcaaaaaggg gatgcgtgat ttgcgcatca actagggtgg aaccgcggga gctacgctct       180
cgtccctag                                                               189

<210> SEQ ID NO 8
<211> LENGTH: 183
<212> TYPE: DNA
<213> ORGANISM: Bacillus subtilis

<400> SEQUENCE: 8
tattattaaa tatgttgcag tgagagaaag aagtacttgc gtttacctca tgaaagcgac        60
cttagggcgg tgtaagctaa ggatgagcac gcaacgaaag gcattcttga gcaattttaa       120
aaaagaggct gggattttgt tctcagcaac tagggtggaa ccgcgggaga actctcgtcc       180
cta                                                                     183

<210> SEQ ID NO 9
<211> LENGTH: 173
<212> TYPE: DNA
<213> ORGANISM: Clostridium acetobutylicum

<400> SEQUENCE: 9
ataatttaat atctatacaa tgacaaagat agaaattgta ttttcttcaa agagaggctg        60
tggagggtgt aaacggtcaa gaaaattcag tagtggagtc tttcgagtat ttttaaaaga       120
aaagcagggc tattgccaat aagggtggaa ccgcggaagt aatttcgtcc ctt              173

<210> SEQ ID NO 10
<211> LENGTH: 214
<212> TYPE: DNA
<213> ORGANISM: Carboxydothermus hydrogenoformans

<400> SEQUENCE: 10
aattaataat ggattggcag tgaaccggag gagtagctgt gatttcccct aaagagagcc        60
gggggctggt gtgaaccggt agggataaac ggtgaaggcg ccggggagcc ggcaggagga       120
aaccccaagg ggagtaaagc ctgcagagtt ttgaggtggg cctttttgg ccaaccaggg       180 tggaaccgcg gaaggatgcc cctttcgtcc ctgg                                   214

<210> SEQ ID NO 11
<211> LENGTH: 176
<212> TYPE: DNA
<213> ORGANISM: Deinococcus radiodurans

<400> SEQUENCE: 11
ggaggcgttg aaccgcagga gtaccgcgaa gagcccccaa cgagcgagcc tgagacggtg        60
agagtcaggc agggtgaggc gcgacgggaa aggcagcggg gagccacaac cggtctgaaa       120
ggtgctggcg agggccagaa ctggggtgga accgcgcatg tcccgtgcgt ccccgg           176

<210> SEQ ID NO 12
<211> LENGTH: 177
<212> TYPE: DNA
<213> ORGANISM: Enterococcus faecalis
```

```
<400> SEQUENCE: 12
gagaagttaa atacgtacga agaaaaagag aagtaaaaag aaccctctgt taagcgaatc      60
tgggagagtg ggagccagaa acacggaact tttgaaaggc actttggagt acgacaaacg    120
aagctgccga tgaacacatc ggaagtaggg tggaaccgcg ataattattc gtcccta        177

<210> SEQ ID NO 13
<211> LENGTH: 151
<212> TYPE: DNA
<213> ORGANISM: Lactococcus lactis

<400> SEQUENCE: 13
gccttgacaa aatgggaaaa tagagctaga atttataggt agcgactcga agatagtgaa     60
agttcgagaa caataatggc ttaacttaaa actgtaatga acacaaataa agtaaaaaat   120
aaaggtggaa ccgtgcattt gcaccctttg t                                   151

<210> SEQ ID NO 14
<211> LENGTH: 184
<212> TYPE: DNA
<213> ORGANISM: Listeria monocytogenes

<400> SEQUENCE: 14
atatcaacta ataggtacgt tgaaggaaaa tagtaacaaa aagctctatt tttagcgagt     60
ccgggtttgg tgtgagccgg atatttaact tttttgtgaa ggcgttctgg agtacagcga   120
aatcaaggtg ggaattgttt taattccaaa tagggtggaa ccgcgagcta actctcgtcc   180
ctat                                                                 184

<210> SEQ ID NO 15
<211> LENGTH: 164
<212> TYPE: DNA
<213> ORGANISM: Staphylococcus aureus

<400> SEQUENCE: 15
atgtcacaaa acattaatt ttacttgcct ttaaataatc tatcaattgt acagcgagtt      60
aaggatagtg taagcttaac aataagattg gcgcaacgaa tcattttaaa ataaaagcga   120
gtgactacac taatttgggt ggaaccgcgg gttaactcgt ccca                     164

<210> SEQ ID NO 16
<211> LENGTH: 207
<212> TYPE: DNA
<213> ORGANISM: Streptococcus equi

<400> SEQUENCE: 16
tttgtgataa actaaccaat aggaaagaaa atagcaggtt tctgatctaa agcgagctcg     60 ggctggtga gagccgagtg atggtactgc tggttggcgc tttctctaaa gagtaggctc    120
aggtgtttgt agcttgcttg acatctgttt atcaacaaga tcaaatgaag taataaatta   180
gggtggaacc gcgttttgac gcccta                                         207

<210> SEQ ID NO 17
<211> LENGTH: 163
<212> TYPE: DNA
<213> ORGANISM: Streptococcus mutans

<400> SEQUENCE: 17
gttaagaaag agagttttgt ggcgtttctg cagcgaacct gagagagtgt aagtcaggtg     60
aaacaaaata aaggactggc actttctctt ggctaatagc caagctaaca atcagataaa   120
```

```
tgaagtaata aattagggtg gaaccgcgtt tcaaacgccc cta                         163

<210> SEQ ID NO 18
<211> LENGTH: 168
<212> TYPE: DNA
<213> ORGANISM: Streptococcus pneumoniae

<400> SEQUENCE: 18 attttttgata taatagtcag caggaaagaa agtcttatgg cgttcttcaa gcgagcttgg     60
gatagtggga gccaagtagg gcaaaataaa gggctggcgc tttctgtagt attttcaaaa    120
acaatgaagt aataaattag ggtggaaccg cgtttctgac gcccctag                 168

<210> SEQ ID NO 19
<211> LENGTH: 205
<212> TYPE: DNA
<213> ORGANISM: Streptococcus pyogenes

<400> SEQUENCE: 19
gctttatgct aaactagact ctaggaaaaa ggatgcaagt atcttatcta aagcgagttc     60
ggggtagtta gagccgaatg gtaggactgc agattggcgc ttccgtttgg gcagtgtgat   120
taagtatatt tgtcaatatt gcccaaaaag atactatata aatgaagtaa taaattaggg   180
tggaaccgcg ttttgacgcc cctag                                         205

<210> SEQ ID NO 20
<211> LENGTH: 51
<212> TYPE: DNA
<213> ORGANISM: Bacillus subtilis

<400> SEQUENCE: 20
ttgacatttg gtccatcttt ttatatgatc atttattata aaatatgttg c              51

<210> SEQ ID NO 21
<211> LENGTH: 438
<212> TYPE: DNA
<213> ORGANISM: Bacillus subtilis

<400> SEQUENCE: 21
attgatttat attacgaaga atattcggga ttgtatttaa aatcaaagcg cttttttagat    60 caaatggaaa gcatgaaaca tcttatgggt gaaaacaaaa gttgacattt ggtccatctt   120
tttatatgat catttattat aaatatgttg cagtgagag aaagaagtac ttgcgtttac    180
ctcatgaaag cgaccttagg gcggtgtaag ctaaggatga gcacgcaacg aaaggcattc   240
ttgagcaatt ttaaaaaaga ggctgggatt tgttctcag caactagggt ggaaccgcgg    300
gagaactctc gtccctatgt tgcggctgg caagcataga gacgggagtt ttttggttgc    360
tgccgcagtc aacttatgaa agaaaagtgg aggtgcttga atgaatatt caagacatga    420 ttctaacctt gcaaaagc                                                 438

<210> SEQ ID NO 22
<211> LENGTH: 438
<212> TYPE: DNA
<213> ORGANISM: Bacillus subtilis

<400> SEQUENCE: 22
attgatttat attacgaaga atattcggga ttgtatttaa aatcaaagcg cttttttagat    60 caaatggaaa gcatgaaaca tcttatgggt gaaaacaaaa gttgacattt ggtccatctt   120
```

-continued

```
tttatatgat catttattat aaaatatgtt gcagtgagag aaagaagtac ttgcgtttac    180
ctcatgaaag cgaccttagg gcggtgtaag ctaaggatga gcacgcaacg aaaggcattc    240
ttgagcaatt ttaaaaaaga ggctgggatt ttgttctcag caactagggt ggaaccgcgg    300
gagaactctc gtccctatgt tgcggctgg caagcataga gacgggagtt ttttggttgc     360
tgccgcagtc aacttatgaa agaaaagtgg aggtgcttga aatgaatatt caagacatga    420
ttctaacctt gcaaaagc                                                   438
```

<210> SEQ ID NO 23
<211> LENGTH: 75
<212> TYPE: DNA
<213> ORGANISM: Bacillus subtilis

<400> SEQUENCE: 23

```
gcggaagtag ttcagtggta gaacaccacc ttgccaaggt ggggtcgcg ggttcgaatc      60 ccgtcttccg ctcca                                                      75
```

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
attgatctag attacgaaga atattcggga ttgta                                35
```

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
gggtatttaa ttaagctttt gcaaggttag aatca                                35
```

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
ggctggggat ccgtcaacaa tggagg                                          26
```

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
ccgcggaagg ataaagcttc aagtaag                                         27
```

<210> SEQ ID NO 28
<211> LENGTH: 407

<212> TYPE: DNA
<213> ORGANISM: Bacillus subtilis

<400> SEQUENCE: 28

```
ggctggagat ctgtcaacaa tggaggatta aaaggcggcg ttgacacagg attttattta      60
tgttaaaaat gatatagctt catatgaaaa ggtaaagatt gagacaagta gaatatcctt     120
acgttccaga gagctgatgg ccggtgaaaa tcagcacaga cggatatatc gaatacactc     180
atgaaccgct tttgcaaaca aagccggcca ggctttcagt agtgaaagaa cggacctgat     240
ccgttatcag gcaaagtgat aagacgaatg tttgcattct cttattagta gggtggtacc     300
gcgataatca atcgtccctt cgtgtaaacg aagggcgtt ttttattttta attaaaaaag     360
gagctttatc ttatgactaa cttacttgaa gacttatcct tccgcgg                   407
```

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

```
ggctggggat ccgtcaacaa tggagg                                           26
```

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

```
ccgcggaagg ataaagcttc aagtaag                                          27
```

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31

```
taatacgact cactatagga ggggtagcg                                        29
```

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32

```
ggaggggtag cg                                                          12
```

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tggtggaggg gggcagattc g                                                 21

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
taatacgact cactatagcg gaagtagttc agtgg                                  35

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcggaagtag ttcagtgg                                                     18

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tggagcggaa gacgggattc gaac                                              24

<210> SEQ ID NO 37
<211> LENGTH: 85
<212> TYPE: DNA
<213> ORGANISM: Bacillus subtilis

<400> SEQUENCE: 37
ggaggggtag cgaagtggct aaacgcggcg gactgtaaat ccgctccctc agggttcggc       60
agttcgaatc tgcccccctc cacca                                             85